(12) United States Patent
Hasegawa et al.

(10) Patent No.: US 8,110,394 B2
(45) Date of Patent: Feb. 7, 2012

(54) CULTURE MICROSCOPE APPARATUS

(75) Inventors: Kazuhiro Hasegawa, Hachioji (JP);
Kenichi Koyama, Sagamihara (JP);
Atsuhiro Tsuchiya, Hachioji (JP);
Atsushi Yonetani, Tama (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/776,182

(22) Filed: May 7, 2010

(65) Prior Publication Data

US 2010/0208053 A1 Aug. 19, 2010

Related U.S. Application Data

(63) Continuation of application No. 10/969,464, filed on Oct. 20, 2004, now Pat. No. 7,799,559.

(30) Foreign Application Priority Data

Oct. 24, 2003 (JP) ................. 2003-365025
May 12, 2004 (JP) ................. 2004-142635

(51) Int. Cl.
*C12M 1/34* (2006.01)
*G02B 21/26* (2006.01)

(52) U.S. Cl. .................. 435/288.7; 435/303.1; 435/809; 359/395; 359/809

(58) Field of Classification Search ............... 435/287.3, 435/288.7, 303.1, 809; 359/395, 398, 809, 359/820
See application file for complete search history.

(56) References Cited

U.S. PATENT DOCUMENTS

| | | | |
|---|---|---|---|
| 4,090,921 A | 5/1978 | Sawamura et al. | |
| 4,629,862 A | 12/1986 | Kitagawa et al. | |
| 4,800,164 A | 1/1989 | Bisconte | |
| 6,008,010 A | 12/1999 | Greenberger et al. | |
| 6,980,293 B1 | 12/2005 | Harada | |

FOREIGN PATENT DOCUMENTS

| | | |
|---|---|---|
| DE | 39 24 701 A1 | 1/1991 |
| DE | 202 14 480 U1 | 1/2003 |
| JP | 60-156996 U | 10/1985 |
| JP | 10-28576 A | 2/1998 |
| JP | 11-084260 A | 3/1999 |
| JP | 2003-93041 A | 4/2003 |
| JP | 2003-093041 A | 4/2003 |
| JP | 2003-107364 A | 4/2003 |

OTHER PUBLICATIONS

Japanese Office Action dated Sep. 14, 2010 (and English translation thereof) in counterpart Japanese Application No. 2004-142635.

*Primary Examiner* — William H Beisner
(74) *Attorney, Agent, or Firm* — Holtz, Holtz, Goodman & Chick, PC

(57) ABSTRACT

A culture microscope apparatus has an illumination unit to apply excitation light to the specimen, a specimen observing portion to observe light generated from the specimen due to the excitation light, and a dimmer unit to dim the excitation light that has penetrated the specimen.

7 Claims, 13 Drawing Sheets

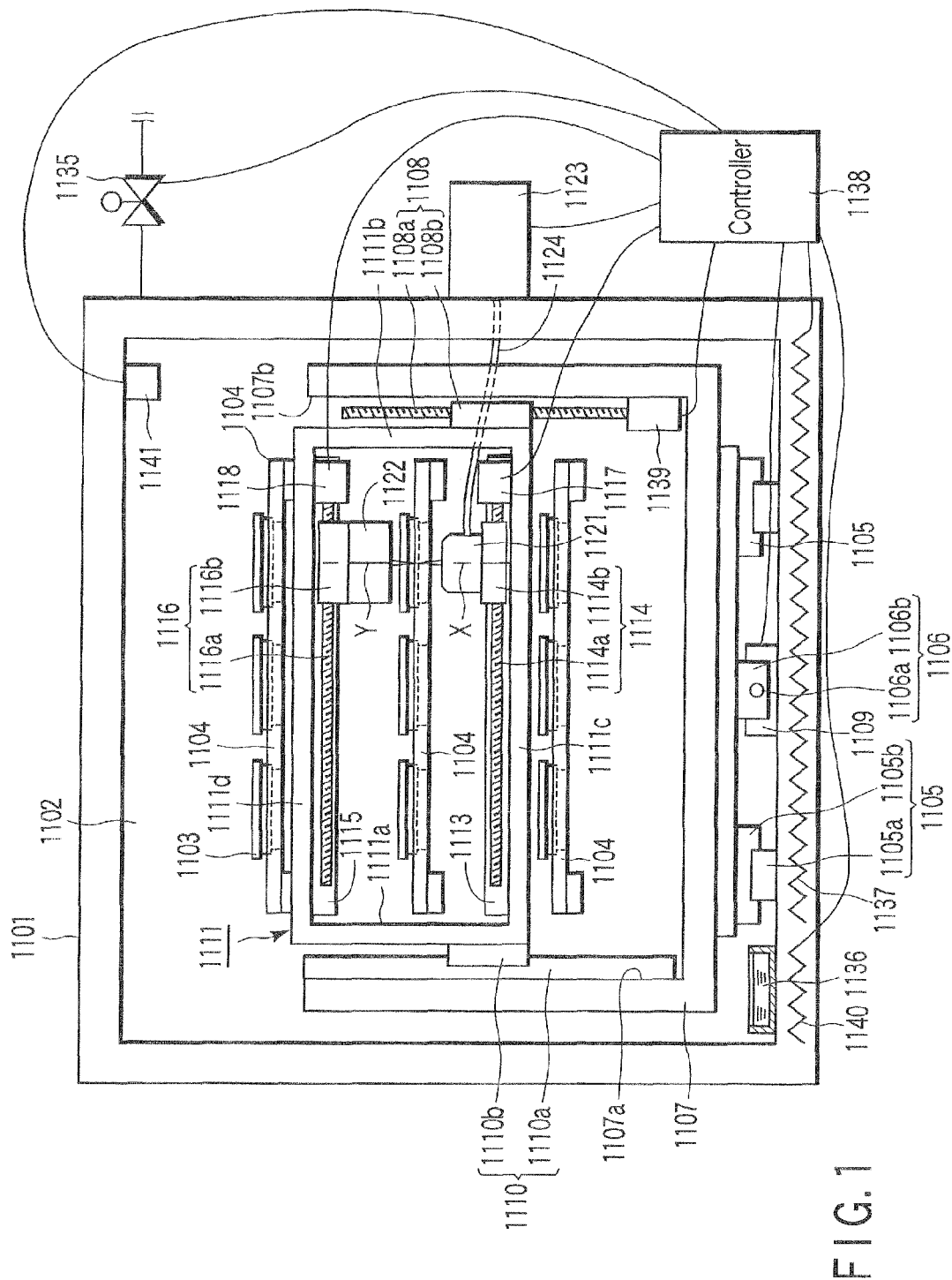
F I G. 1 ic # CULTURE MICROSCOPE APPARATUS

CROSS-REFERENCE TO RELATED APPLICATIONS

The present application is a Continuation Application of U.S. application Ser. No. 10/969,464 filed Oct. 20, 2004, now U.S. Pat. No. 7,799,559, which claims the benefit of priority from prior Japanese Patent Applications No. 2003-365025, filed Oct. 24, 2003; and No. 2004-142635, filed May 12, 2004, the entire contents of all of which are incorporated herein by reference.

BACKGROUND OF THE INVENTION

1. Field of the Invention

The present invention relates to a culture microscope apparatus to observe living cells that have been kept alive under a constant environmental condition for long-term observation of cells of living organisms such as animals or plants.

2. Description of the Related Art

Generally, in such fields as biochemistry, living cells of animals or plants are kept alive under a suitable condition to observe behavior of the living cells for functional analysis of living organisms.

For the behavioral observation of living cells, fluorescent dyes using antigen antibody reactions and fluorescent observation using gene-transferred fluorescent protein are utilized. The fluorescent observation is used because it enables observation on the molecular level and behavioral observation of distributions and molecules. It is to be noted here that the fluorescence is a phenomenon in which if energy such as ultraviolet rays is applied to a substance from the outside, atoms of the substance transit from ground state to excited state and then emit specific light when returning to the ground state. The ultraviolet rays from the outside are generally called excitation light.

On the other hand, there is a phenomenon called discoloration in which if the fluorescent dyes and the fluorescent protein are continuously exposed to the excitation light, the intensity of fluorescence light is gradually lowered or nullified. Therefore, the fluorescent observation requires attention, for example, using as weak excitation light as possible and exposing a sample to the excitation light during observation only.

BRIEF SUMMARY OF THE INVENTION

The present invention is directed, according to an aspect of the invention, to a culture microscope apparatus that reduces discoloration of fluorescent dyes. The culture microscope apparatus according to the present invention comprises illumination means for applying excitation light to a specimen, specimen observing means for observing light generated from the specimen due to the excitation light, and dimmer means for dimming the excitation light that has penetrated the specimen.

The present invention is directed, according to another aspect of the invention, to a culture microscope apparatus that has less temperature changes in an installation environment and is easily cleaned. The culture microscope apparatus according to the present invention comprises a microscope device to observe a specimen, a culture device capable of controlling temperature and humidity, and isolation means for isolating the microscope device from moisture of the culture device.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 shows a schematic configuration of a first embodiment of the present invention;

DETAILED DESCRIPTION OF THE INVENTION

First Embodiment

Figure 7:
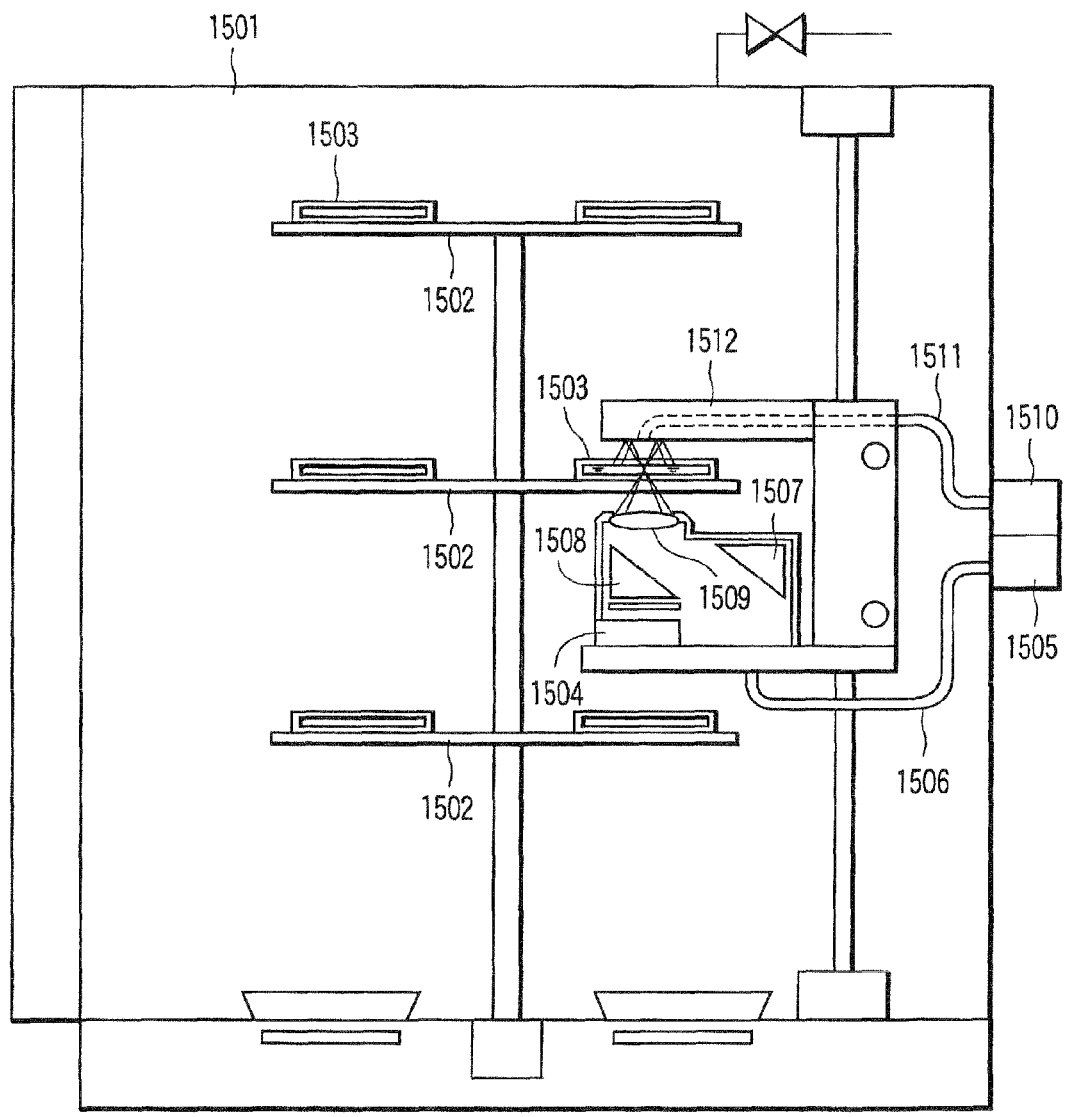
FIG. 7 shows a schematic configuration of a conventional culture microscope apparatus.

FIG. 7 shows a schematic configuration of a conventional culture microscope apparatus disclosed in Jpn. Pat. Appln. KOKAI Publication No. 2003-93041. In this culture microscope apparatus, living samples contained in culture cases 1503 placed on sample tables 1502 in a culture container 1501 are cultured in the culture container 1501, and images of the living samples are picked up by a CCD 1504 for observation. In order to observe fluorescent images of the living samples, light from a fluorescence measurement excitation light source 1505 is projected from an excitation light projection fiber 1506, reflected by mirrors 1507 and 1508, and applied as excitation light through objective lens 1509 to the living sample in the culture case 1503, and then an image of fluorescence light emitted from the living sample is picked up by the CCD 1504 through the objective lens 1509. On the other hand, for observation of transmitted light image of the living sample, light from a white light source 1510 is applied to the living sample in the culture case 1503 through a white light projection fiber 1511, and an image of light that has penetrated the living sample is picked up by the CCD 1504 through the objective lens 1509.

In the culture microscope apparatus of Jpn. Pat. Appln. KOKAI Publication No. 2003-93041, most of the excitation light that has been projected from the excitation light projection fiber 1506 and applied through the objective lens 1509 to the living sample in the culture case 1503 may penetrate the culture case 1503 and be reflected by the surface of a fixed arm 1512 supporting an projection end of the fiber 1511, so that the reflected excitation light might excite the living samples that are not targeted for observation to fade fluorescent dyes. Further, even if all the excitation light that has penetrated the culture case 1503 can be captured by the white light projection fiber 1511, light reflected by a lamp of the white light source 1510 or the like may return through the white light projection fiber 1511 to fade the fluorescent dyes.

In view of such circumstances, the present embodiment is directed to a culture microscope apparatus that reduces the discoloration of the fluorescent dyes.

Figure 2:
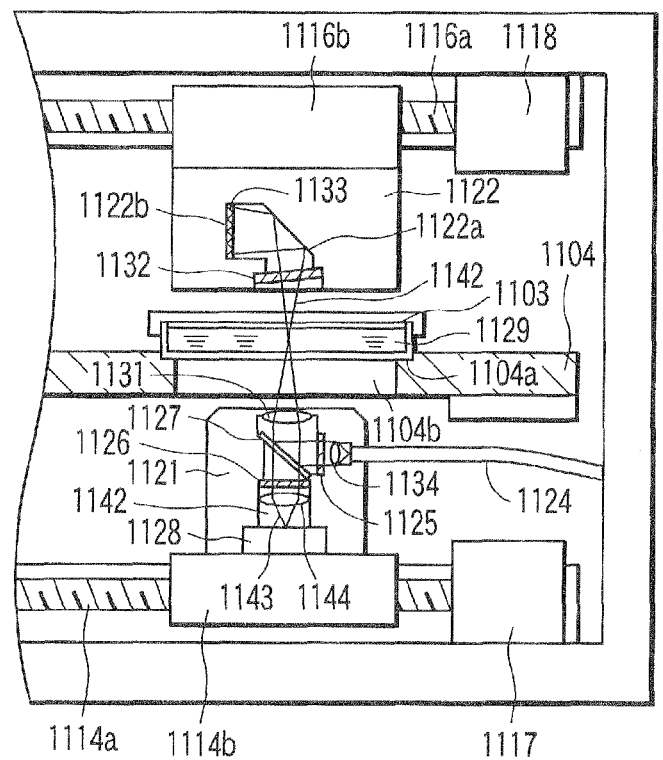
FIG. 2 shows a schematic configuration of essential parts of the first embodiment.

FIG. 1 shows a schematic configuration of the culture microscope apparatus to which the present invention is applied, and FIG. 2 shows an enlarged schematic configuration of essential parts of the culture microscope apparatus.

A culture microscope apparatus body 1101 is provided with a culture container 1102. The culture container 1102 is provided with multistage (three stages in an example shown) culture case support racks 1104. Each of the culture case support racks 1104 supports (three in an example shown) specimens (i.e., culture cases 1103 containing living cells 1129). The culture case support rack 1104 is provided with a recess 1104a slightly larger than the culture case 1103, and an opening 1104b slightly smaller than the culture case 1103 on a bottom surface of the recess 1104a, as shown in FIG. 2. Thus, the culture case support rack 1104 uses the recess 1104a to position the culture case 1103 and allows of observation of the living cells 1129 in the culture case 1103 through the opening 1104b.

Here, the culture case 1103 comprises, for example, a dish and a micro well-plate to which a culture solution is added, and a necessary amount of living cells 1129 is distributed and contained in the culture case 1103. Further, the culture case 1103 is made of a resin material to which a colorless and transparent glass is affixed or in which a glass is affixed on its bottom surface.

A valve 1135 is connected to the culture container 1102. This valve 1135 is for supplying carbon dioxide into the culture container 1102. A temperature adjustment heater 1137 for temperature adjustment and an evaporating dish 1136 retaining water are located on the bottom surface of the culture container 1102, and a humidification heater 1140 is located under the evaporating dish 1136. Further, a sensor 1141 is provided in the culture container 1102. This sensor 1141 is intended to detect carbon dioxide concentration, humidity and temperature in the culture container 1102.

A controller 1138 is connected to the valve 1135, the temperature adjustment heater 1137, the humidification heater 1140 and the sensor 1141. The controller 1138 is intended to perform various kinds of control; for example, if the carbon dioxide concentration, humidity and temperature in the culture container 1102 are detected by the sensor 1141, the controller 1138 opens the valve 1135 in accordance with an output of the detection to supply carbon dioxide, turns on the humidification heater 1140 to evaporate water from the evaporating dish 1136 for supply of steam, or turns on the temperature adjustment heater 1137 to supply heat for adjustment of temperature in the culture container 1102. This maintains a constant environmental condition in the culture container 1102 necessary for the living cells 1129 so that the living cells 1129 can stay alive for a long period of time in the culture container 1102.

On the other hand, a pair of first guides 1105 and a first movement screw 1106 are arranged on the bottom surface of the culture container 1102 in parallel in a direction perpendicular to the drawing.

The first guide 1105 has a fixed portion 1105a and a moving portion 1105b, and the moving portion 1105b is linearly movable in contrast with the fixed portion 1105a. The first movement screw 1106 has a screw portion 1106a and a nut portion 1106b, and the screw portion 1106a is turned while the rotation of the nut portion 1106b is regulated so that the nut portion 1106b moves straight.

A first moving part 1107 is attached to the moving portion 1105b of the first guide 1105 and the nut portion 1106b of the first movement screw 1106. Further, a first drive portion 1109 is attached to the screw portion 1106a of the first movement screw 1106. The first drive portion 1109 rotationally drives the screw portion 1106a of the first movement screw 1106 under instructions from the controller 1138, and the rotation of the screw portion 1106a is converted to straight movement of the nut portion 1106b, thereby enabling the first moving part 1107 to move in a direction (direction perpendicular to the drawing) guided by the first guide 1105.

In the first moving part 1107, a pair of guide mounting surfaces 1107a, 1107b is provided to face each other perpendicularly to the bottom surface of the culture container 1102. The guide mounting surface 1107a is provided with a second guide 1110, and the guide mounting surface 1107b is provided with a second movement screw 1108. The second guide 1110 and the second movement screw 1108 are configured in the same manner as the first guide 1105 and the first movement screw 1106. In other words, the second guide 1110 has a fixed portion 1110a fixed to the guide mounting surface 1107a and a moving portion 1110b, and allows the moving portion 1110b to move linearly relative to the fixed portion 1110a. Further, the second movement screw 1108 has a screw portion 1108a fixed to the guide mounting surface 1107a and a nut portion 1108b, and the screw portion 1108a is turned so that the nut portion 1108b moves straight.

A second moving part 1111 is attached to the moving portion 1110b of the second guide 1110 and the nut portion 1108b of the second movement screw 1108. Further, a second drive portion 1139 is attached to the screw portion 1108a of the second movement screw 1108. The second drive portion 1139 rotationally drives the screw portion 1108a of the second movement screw 1108 under instructions from the controller 1138, and the rotation of the screw portion 1108a is converted to straight movement of the nut portion 1108b, thereby enabling the second moving part 1111 to move in a direction (vertical direction of the drawing) guided by the second guide 1110.

The second moving part 1111 is made from a rectangular frame, and has longitudinal portions 1111a, 1111b along the guide mounting surfaces 1107a, 1107b and guide support portions 1111c, 1111d parallel with the culture case support rack 1104.

The guide support portion 1111c is provided with a third guide 1113 and a third movement screw 1114, and the guide support portion 1111d is provided with a fourth guide 1115 and a fourth movement screw 1116. The third guide 1113 and the fourth guide 1115 are configured in the same manner as the first guide 1105. The third movement screw 1114 and the fourth movement screw 1116 are also configured in the same manner as the first movement screw 1106. Here, the third movement screw 1114 has a screw portion 1114a fixed to the guide support portion 1111c and a nut portion 1114b, and the screw portion 1114a is turned so that the nut portion 1114b moves straight. The fourth movement screw 1116 also has a screw portion 1116a to the guide support portion 1111d and a nut portion 1116b, and the screw portion 1116a is turned so that the nut portion 1116b moves straight.

Specimen observing means or a specimen observing portion 1121 is attached to the nut portion 1114b of the third movement screw 1114. Further, a third drive portion 1117 is attached to the screw portion 1114a of the third movement screw 1114. The third drive portion 1117 rotationally drives the screw portion 1114a of the third movement screw 1114 under instructions from the controller 1138, and the rotation of the screw portion 1114a is converted to straight movement of the nut portion 1114b, thereby enabling the specimen observing portion 1121 to move in accordance with the third guide 1113 in a direction (horizontal direction of the drawing) along the culture case support rack 1104.

Dimmer means or a dimmer unit 1122 is attached to the nut portion 1116b of the fourth movement screw 1116. Further, a fourth drive portion 1118 is attached to the screw portion 1116a of the fourth movement screw 1116. The fourth drive portion 1118 rotationally drives the screw portion 1116a of the fourth movement screw 1116 under instructions from the controller 1138, and the rotation of the screw portion 1116a is converted to straight movement of the nut portion 1116b, thereby enabling the dimmer means or dimmer unit 1122 to move in accordance with the fourth guide 1115 in a direction (horizontal direction of the drawing) along the culture case support rack 1104.

In this case, the controller 1138 simultaneously drives the third movement screw 1114 by the third drive portion 1117 and the fourth movement screw 1116 by the fourth drive portion 1118, and controls so that the specimen observing portion 1121 faces the dimmer means or dimmer unit 1122 with the culture case 1103 put between them and an optical axis X of the specimen observing portion 1121 coincides with an optical axis Y of the dimmer means or dimmer unit 1122.

The specimen observing portion 1121 is connected with Illumination means or an illumination unit. The illumination means or illumination unit includes an incident-light fiber 1124 and an external illumination portion 1123. The specimen observing portion 1121 is connected to the external illumination portion 1123 through the incident-light fiber 1124. The external illumination portion 1123 comprises a mercury lamp, a xenon lamp, a laser light source or the like.

The specimen observing portion 1121 has, as an observation optical system to observe the living cells 1129 in the culture case 1103, a first lens 1134, an excitation filter 1125, an objective lens 1131, a dichroic mirror 1127, an emission filter 1126 and an image-forming lens 1144, and also has image pickup means or an image pickup device 1128 such as a CCD. Here, the excitation filter 1125 has properties that only transmit wavelengths necessary for the excitation of the fluorescent dyes. The dichroic mirror 1127 has properties that reflect the excitation light having a relatively short wavelength and transmit the relatively fluorescence light having a long wavelength. Moreover, the emission filter 1126 has properties that selectively transmit the fluorescence light emitted by the fluorescent dyes.

Furthermore, if illumination light from the external illumination portion 1123 is introduced to the specimen observing portion 1121 through the incident-light fiber 1124, the light projected from the incident-light fiber 1124 will be light converging on a rear focal plane of the objective lens 1131 through the first lens 1134, and the light is selected by the excitation filter 1125, reflected by the dichroic mirror 1127 and converges on the rear focal plane of the objective lens 1131. Further, the light converging on the rear focal plane of the objective lens 1131 is brought into parallel light by the objective lens 1131 to illuminate an illumination range uniformly as excitation light 1142 that excites the fluorescent dyes in the living cells 1129 in the culture case 1103. The fluorescent dyes excited by the excitation light 1142 emit fluorescence light 1143 having a wavelength longer than that of the excitation light 1142. The fluorescence light 1143 is brought into parallel light by the objective lens 1131, penetrates the dichroic mirror 1127 and the emission filter 1126, and falls on an image pickup plane of the image pickup device 1128 through the image-forming lens 1144, thereby picking up an image thereof.

Meanwhile, the illumination range is dotted with the living cells 1129, and parts to be observed within the living cells 1129 are further limited and less. Thus, most of the excitation light 1142 in the illumination range penetrates the culture case 1103 to arrive at the dimmer means or dimmer unit 1122.

The dimmer means or dimmer unit 1122 has a sealing glass 1132, a reflective member 1122a and a light absorption member 1122b to dim the excitation light penetrating the culture case 1103. In this case, the sealing glass 1132 is installed obliquely with respect to the optical axis X of the specimen observing portion 1121 so that the excitation light 1142 penetrating the culture case 1103 is reflected by the surface of the sealing glass 1132 and the reflected light will not return to the side of the living cells 1129. The reflective member 1122a is located with a normal at 45 degrees to the optical axis Y so that the excitation light 1142 penetrating the sealing glass 1132 is reflected perpendicularly to the optical axis Y. The light absorption member 1122b is located on a reflected light path of the reflective member 1122a. For example, a hair transplant paper 1133 is attached to the light absorption member 1122b to absorb the excitation light.

In such a configuration, the first moving part 1107 is moved back and forth along the first guide 1105 by the first movement screw 1106 and the second moving part 1111 is moved up and down along the second guide 1110 by the second movement screw 1108 in order to set the height positions of the specimen observing portion 1121 and the dimmer means or dimmer unit 1122 relative to the respective culture case support racks 1104. Moreover, the third movement screw 1114 and the fourth movement screw 1116 are driven so that the specimen observing portion 1121 and the dimmer means or dimmer unit 1122 move along the culture case support racks 1104 in order to position the specimen observing portion 1121 and the dimmer means or dimmer unit 1122 above the living cells 1129 in the culture case 1103 on the culture case support rack 1104. In this case, the specimen observing portion 1121 and the dimmer means or dimmer unit 1122 are set in such a state that the optical axis X of the specimen observing portion 1121 coincides with the optical axis Y of the dimmer means or dimmer unit 1122 so that the living cells 1129 in the culture case 1103 are placed between them.

In this state, if the illumination light from the external illumination portion 1123 is introduced to the specimen observing portion 1121 through the incident-light fiber 1124, the light projected from the incident-light fiber 1124 will be light converging on the rear focal plane of the objective lens 1131 through the first lens 1134, and the light is selected by the excitation filter 1125, reflected by the dichroic mirror 1127 and converges on the rear focal plane of the objective lens 1131. The light converging on the rear focal plane of the objective lens 1131 is brought into parallel light by the objective lens 1131 to illuminate the illumination range uniformly as excitation light 1142 that excites the fluorescent dyes in the living cells 1129 in the culture case 1103. The fluorescent dyes excited by the excitation light 1142 emit the fluorescence light 1143 having a wavelength longer than that of the excitation light 1142. The fluorescence light 1143 is brought into the parallel light by the objective lens 1131, penetrates the dichroic mirror 1127 and the emission filter 1126, and falls on the image pickup plane of the image pickup device 1128 through the image-forming lens 1144, thereby picking up an image thereof.

On the other hand, the excitation light 1142 that penetrates the culture case 1103 and that is not used for excitation reaches the dimmer means or dimmer unit 1122 and falls on the sealing glass 1132. In this case, as the sealing glass 1132 is provided obliquely with respect to the optical axis X of the specimen observing portion 1121, a slight amount of reflection on the surface of the sealing glass 1132 returns to the observed parts of the living cells 1129 without causing uneven illumination. Further, the excitation light 1142 that has penetrated the sealing glass 1132 is reflected by the reflective member 1122a, reaches the light absorption member 1122b and is absorbed by the hair transplant paper 1133.

Therefore, the excitation light 1142 that has penetrated the culture case 1103 and that is not used for excitation is led to and dimmed by the dimmer means or dimmer unit 1122 without returning to the side of the living cells 1129, thereby making it possible to significantly reduce the discoloration of the fluorescent dyes in the living cells 1129 that are not targeted for observation. This allows the fluorescent image with good contrast to be observed for a long period of time.

Furthermore, since the hair transplant paper 1133 used for the dimmer means or dimmer unit 1122 is sealed in the dimmer means or dimmer unit 1122 by the sealing glass 1132, it is also possible to prevent contamination inside the culture container 1102.

Second Embodiment

Next, a second embodiment of the present invention will be described. The present embodiment is directed to another dimmer unit applicable instead of the dimmer unit of the first embodiment. Therefore, as the culture microscope apparatus to which the present embodiment is applied is similar to that described with reference to FIG. 1, FIG. 1 is incorporated herein.

Figure 3:
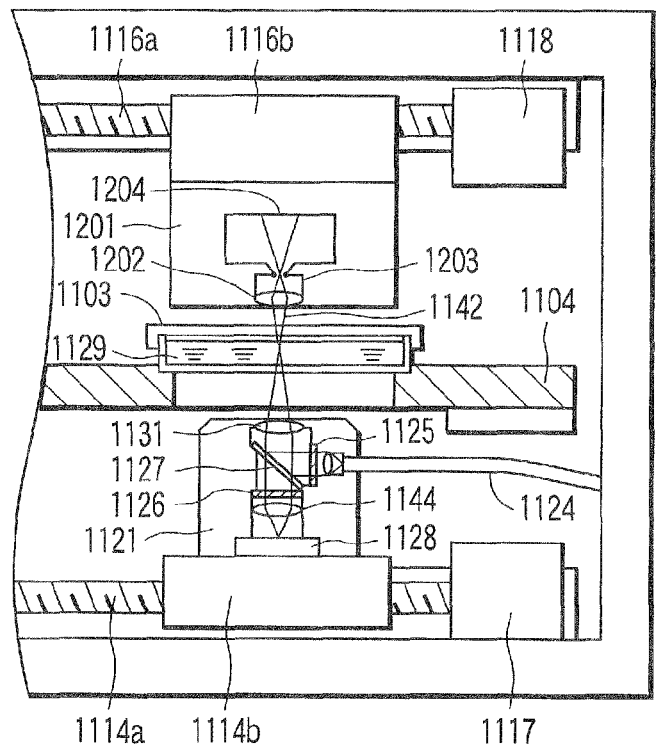
FIG. 3 shows a schematic configuration of essential parts of a second embodiment of the present invention.

FIG. 3 shows a schematic configuration of essential parts of the culture microscope apparatus of the present invention. In FIG. 3, the same numerals are given to the same parts as those in FIG. 2.

Dimmer means or a dimmer unit 1201 in the present embodiment has a second lens 1202, a pin hole 1203 and a scattering portion 1204. The pin hole 1203 is set greater than the diameter of the excitation light 1142 converged by the second lens 1202. The scattering portion 1204 absorbs and scatters the incident excitation light 1142 and has low reflecting coating inside.

In such a configuration, the excitation light 1142 penetrating the culture case 1103 is converged into the pin hole 1203 by the second lens 1202. The light that has passed through the pin hole 1203 enters the scattering portion 1204. The scattering portion 1204 absorbs and scatters the incident excitation light 1142 with the low reflecting coating therein.

Thus, the excitation light 1142 is repeatedly absorbed and scattered in the scattering portion 1204 such that it is progressively dimmed to reduce energy. In this case, the excitation light repeatedly reaches the pin hole 1203 several times, thereby making it possible to sufficiently reduce damage to the living cells 1129 even if part of the light returns to the living cells 1129.

Again, in this case, if the above-mentioned hair transplant paper 1133 is provided in the scattering portion 1204 and the sealing glass 1132 described in detail is provided in the pin hole 1203, the degree of dimming can be increased while the contamination of the living cells 1129 is reduced.

Third Embodiment

Next, a third embodiment of the present invention will be described. The present embodiment is directed to another dimmer unit applicable instead of the dimmer unit of the first embodiment. Therefore, as the culture microscope apparatus to which the present embodiment is applied is similar to that described with reference to FIG. 1, FIG. 1 is incorporated herein.

Figure 4:
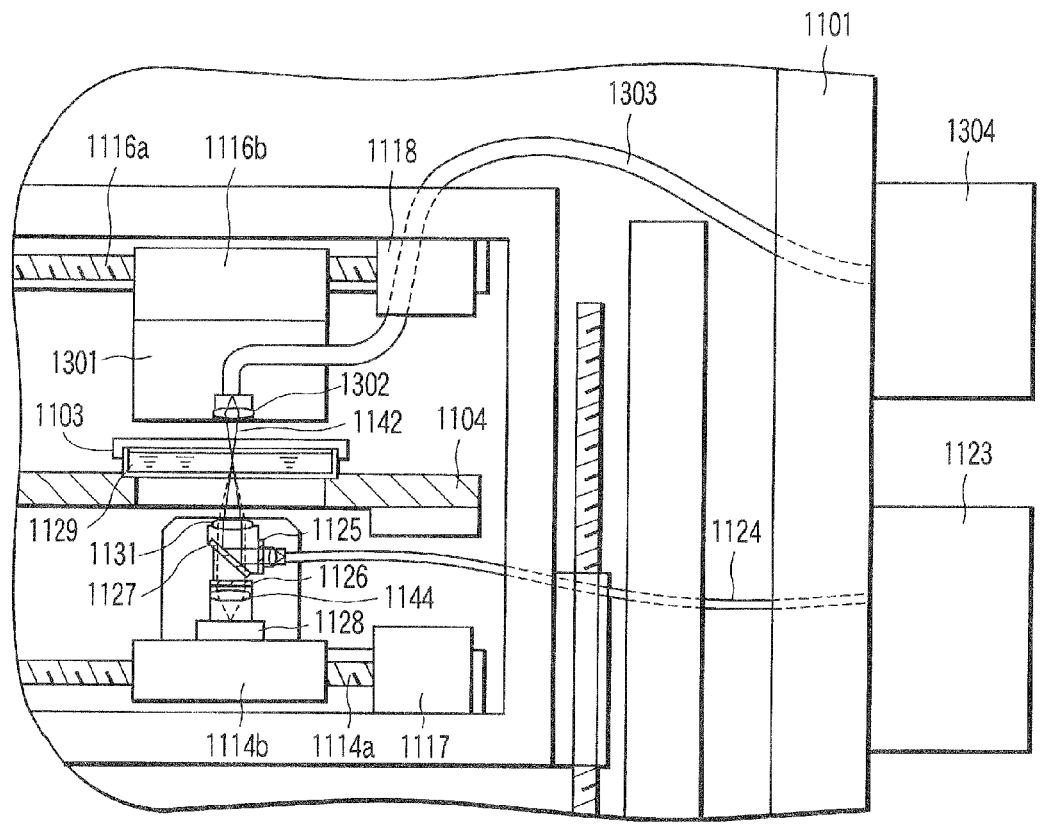
FIG. 4 shows a schematic configuration of essential parts of a third embodiment of the present invention.
Figure 5:
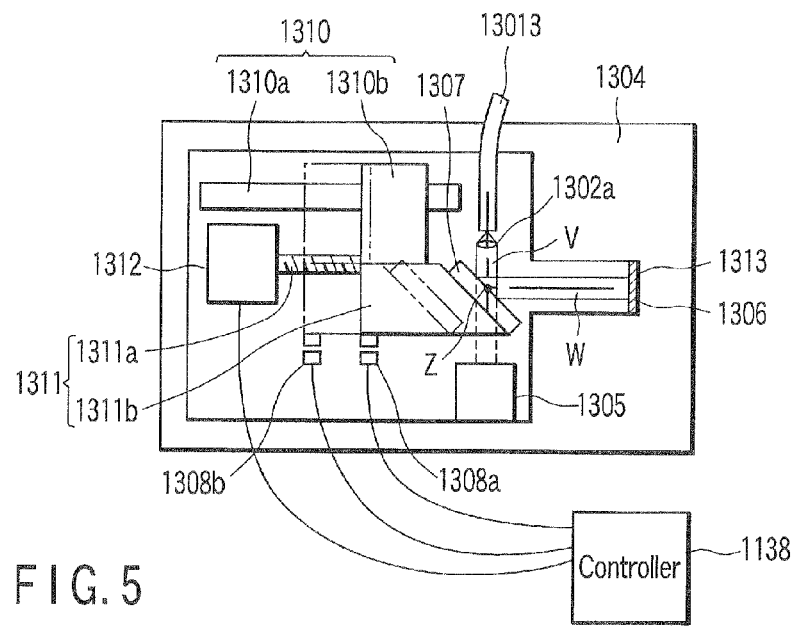
FIG. 5 shows a schematic configuration of an externally installed part used for the third embodiment.

FIG. 4 and FIG. 5 show schematic configurations of essential parts of the culture microscope apparatus of the present invention. In FIG. 4 and FIG. 5, the same numerals are given to the same parts as those in FIG. 2.

Dimmer means or a dimmer unit 1301 in the present embodiment has a third lens 1302 and a transmitted-light fiber 1303, and further has an externally installed part 1304 attached to the culture microscope apparatus body 1101. The third lens 1302 converges the excitation light 1142 that has penetrated the living cells 1129 to an end of the transmitted-light fiber 1303. The transmitted-light fiber 1303 transmits the excitation light 1142 introduced through the third lens 1302 to the externally installed part 1304.

In the externally installed part 1304, a lens 1302a and an illumination light source 1305 are located on an optical axis V at an end of the transmitted-light fiber 1303, as shown in FIG. 5. A dimmer portion 1306 is located on an optical axis W vertical to the optical axis V at the end of the transmitted-light fiber 1303. A reflecting mirror 1307 is located at an intersecting point Z of the optical axis V and the optical axis W. The reflecting mirror 1307 is located to form an angle of 45° to the optical axes V, W and is movable in a direction of the optical axis W.

The reflecting mirror 1307 is provided with a fifth guide 1310 and a fifth movement screw 1311. The fifth guide 1310 has a fixed portion 1310a fixed to the side of the externally installed part 1304 and a moving portion 1310b, and allows the moving portion 1310b to move linearly relative to the fixed portion 1310a. Further, the fifth movement screw 1311 has a screw portion 1311a fixed, in a manner to be able to turn, to the side of the externally installed part 1304 and a nut portion 1311b, and the screw portion 1311a is turned so that the nut portion 1311b moves straight.

The reflecting mirror 1307 is attached to the moving portion 1310b of the fifth guide 1310 and the nut portion 1311b of the fifth movement screw 1311. Further, a fifth drive portion 1312 is attached to the screw portion 1311a of the fifth movement screw 1311. The fifth drive portion 1312 rotationally drives the screw portion 1311a of the fifth movement screw 1311 under instructions from the controller 1138, and the rotation of the screw portion 1311*a* is converted to straight movement of the nut portion 1311*b*, thereby enabling the reflecting mirror 1307 to move in a direction (direction of the optical axis W) guided by the fifth guide 1310.

Position sensors 1308*a*, 1308*b* are located on a travel path of the reflecting mirror 1307. The position sensor 1308*a* detects that the reflecting mirror 1307 is located at the intersecting point Z of the optical axis V and the optical axis W, and the position sensor 1308*b* detects that the reflecting mirror 1307 is located, on the optical axis W, at an evacuated position where it does not prevent the excitation light projected from the transmitted-light fiber 1303. Thereby, the controller 1138 can control the position of the reflecting mirror 1307 by use of the detected positions of the position sensors 1308*a*, 1308*b*, so that an optical connection end of the transmitted-light fiber 1303 can be switched between the dimmer portion 1306 and the illumination light source 1305.

According to such a configuration, when the reflecting mirror 1307 is located at the intersecting point Z, the excitation light 1142 projected from the transmitted-light fiber 1303 is brought into parallel light by the lens 1302*a*, and is reflected by the reflecting mirror 1307 and reaches the dimmer portion 1306. In this case, again, if the above-mentioned hair transplant paper 1133 is provided in the dimmer portion 1306, the excitation light 1142 is absorbed and dimmed by the hair transplant paper 1133.

On the other hand, when the reflecting mirror 1307 is moved to the evacuated position on the optical axis W where it does not prevent the excitation light projected from the transmitted-light fiber 1303, the transmitted-light fiber 1303 is optically connected to the illumination light source 1305, so that the light from the illumination light source 1305 is projected from the third lens 1302 through the transmitted-light fiber 1303, and is applied to the living cells 1129 from the opposite side of the specimen observing portion 1121 with reference to the living cells 1129.

Thus, the position of the reflecting mirror 1307 can be switched to lead the excitation light 1142 that has penetrated the culture case 1103 to the side of the dimmer portion 1306 for dimming in the case of incident-light illumination so that the discoloration of the living cells 1129 can be prevented. On the one hand, if the light from the illumination light source 1305 illuminates the living cells 1129 at the time of transmitted-light illumination, a transmitted image of the living cells 1129 can be observed.

Fourth Embodiment

Next, a fourth embodiment of the present invention will be described. The present embodiment is directed to another dimmer unit applicable instead of the dimmer unit of the first embodiment. Therefore, as the culture microscope apparatus to which the present embodiment is applied is similar to that described with reference to FIG. 1, FIG. 1 is incorporated herein.

Figure 6:
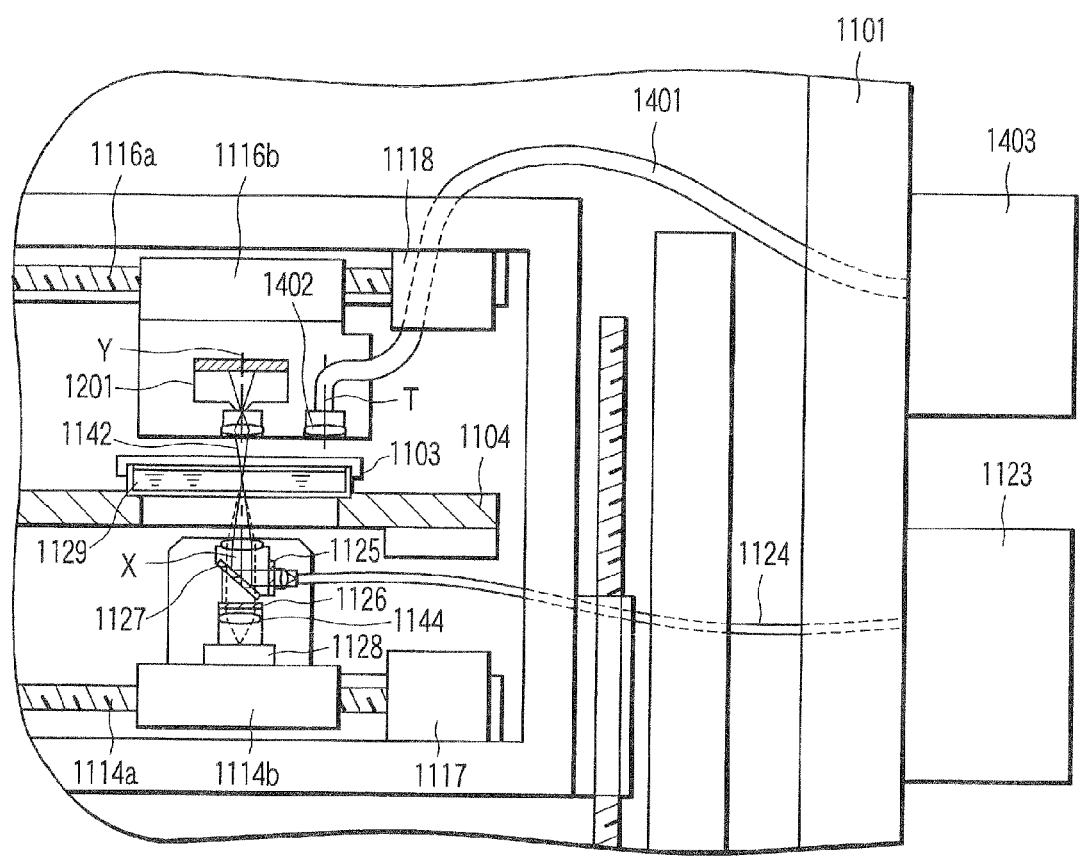
FIG. 6 shows a schematic configuration of essential parts of a fourth embodiment of the present invention.

FIG. 6 shows a schematic configuration of essential parts of the culture microscope apparatus of the present invention. In FIG. 6, the same numerals are given to the same parts as those in FIG. 3.

The culture microscope apparatus of the present embodiment comprises a transmitted-light fiber 1401, a fourth lens 1402 and an externally provided illumination light source 1403, in addition to the dimmer means or dimmer unit 1201 described in the second embodiment. The illumination light source 1403 is optically connected to the fourth lens 1402 through the transmitted-light fiber 1401, and light from the illumination light source 1403 is projected from the fourth lens 1402 through the transmitted-light fiber 1401.

According to such a configuration, if the optical axis Y of the dimmer means or dimmer unit 1201 is adapted to coincide with the optical axis X of the specimen observing portion 1121, the excitation light 1142 that has penetrated the culture case 1103 is introduced into the dimmer means or dimmer unit 1201 and dimmed.

Furthermore, if the dimmer means or dimmer unit 1201 is moved by the fourth guide 1115, the fourth movement screw 1116 and the fourth drive portion 1118, and an optical axis T on the side of the fourth lens 1402 and the transmitted-light fiber 1401 is adapted to coincide with the optical axis X of the specimen observing portion 1121, the light from the illumination light source 1403 is projected from the fourth lens 1402 through the transmitted-light fiber 1401, and is applied to the living cells 1129 from the opposite side of the specimen observing portion 1121 with reference to the living cells 1129. This enables the living cells 1129 to be illuminated with the light from the illumination light source 1403 to obtain a transmission observation image.

In this way, the excitation light 1142 can be dimmed and observation of the living cells 1129 with transmitted illumination can be performed without specially providing means or a mechanism to switch the position of the reflecting mirror 1307 described in the third embodiment.

Fifth Embodiment

The background of the present embodiment will first be described.

Because living organisms have a high degree of complexity, it is not easy to understand their structures and functions. Therefore, a simple experiment system has recently been utilized, and it uses cells that are minimum units capable of reproducing a life phenomenon, that is, the cultured cells. The cultured cells are used to enable an experiment in which analyses of a hormone response and the like are not affected by other factors in the living organism.

In other words, functional analysis of genes can be implemented by the introduction and inhibition of genes. It is necessary to use an environment simulating the inside of the living organism in order to culture cells. Therefore, the temperature is set at a body temperature of 37° C., and a culture medium simulating intercellular fluid is used. The culture medium includes a carbonic acid buffer for PH adjustment in addition to sources of nutrition such as amino acid. The carbonic acid buffer is in an equilibrium state in the presence of air containing carbon dioxide gas at a high partial pressure of 5%, and used for culture in an open system such as a dish. Moreover, a highly humid environment is required to prevent water from evaporating from the culture medium.

To culture cells, a carbon dioxide gas incubator that has the above-mentioned environmental conditions is used.

A phase contrast microscope is used to observe the state of cells and a fluorescence microscope is used to observe the expression of GFP, thereby performing time-lapse observation based on time-series image acquisition.

However, the microscope is generally placed outside the carbon dioxide gas incubator, the observation causes changes in, for example, temperature and PH to cells to give stress to the cells, which might affect an experimental result.

Therefore, Jpn. Pat. Appln. KOKAI Publication No. 2003-93041 proposes an apparatus in which a movable device and a microscope are arranged in an incubator capable of controlling carbon dioxide gas, temperature and humidity. This apparatus makes it possible to observe cells in a culture environment without taking the cultured cells from the culture environment.

Furthermore, Jpn. Pat. Appln. KOKAI Publication No. 10-28576 proposes a microscopic observation transparent constant temperature culture apparatus that is installed on a microscope and that can control carbon dioxide gas, temperature and humidity.

If the cultured cells are contaminated with microorganisms such as bacteria and molds having a high proliferation rate, the cultured cells run out of nutrients and die. Culture instruments are disinfected and sterilized for prevention of contamination, but the apparatus of Jpn. Pat. Appln. KOKAI Publication No. 2003-93041 comprises moving means or a moving mechanism in the culture apparatus, thus having a complicated shape in the apparatus and having difficulty in cleaning. This will be a factor that restricts the sufficient prevention of contamination.

Moreover, in the apparatus of Jpn. Pat. Appln. KOKAI Publication No. 10-28576, a container is constructed in a limited space on the microscope, so that temperature setting is easily changed by the atmospheric environment.

In view of such circumstances, the present embodiment is directed to the culture microscope apparatus that causes a small change in an installed environment and that is easily cleaned.

Figure 8:
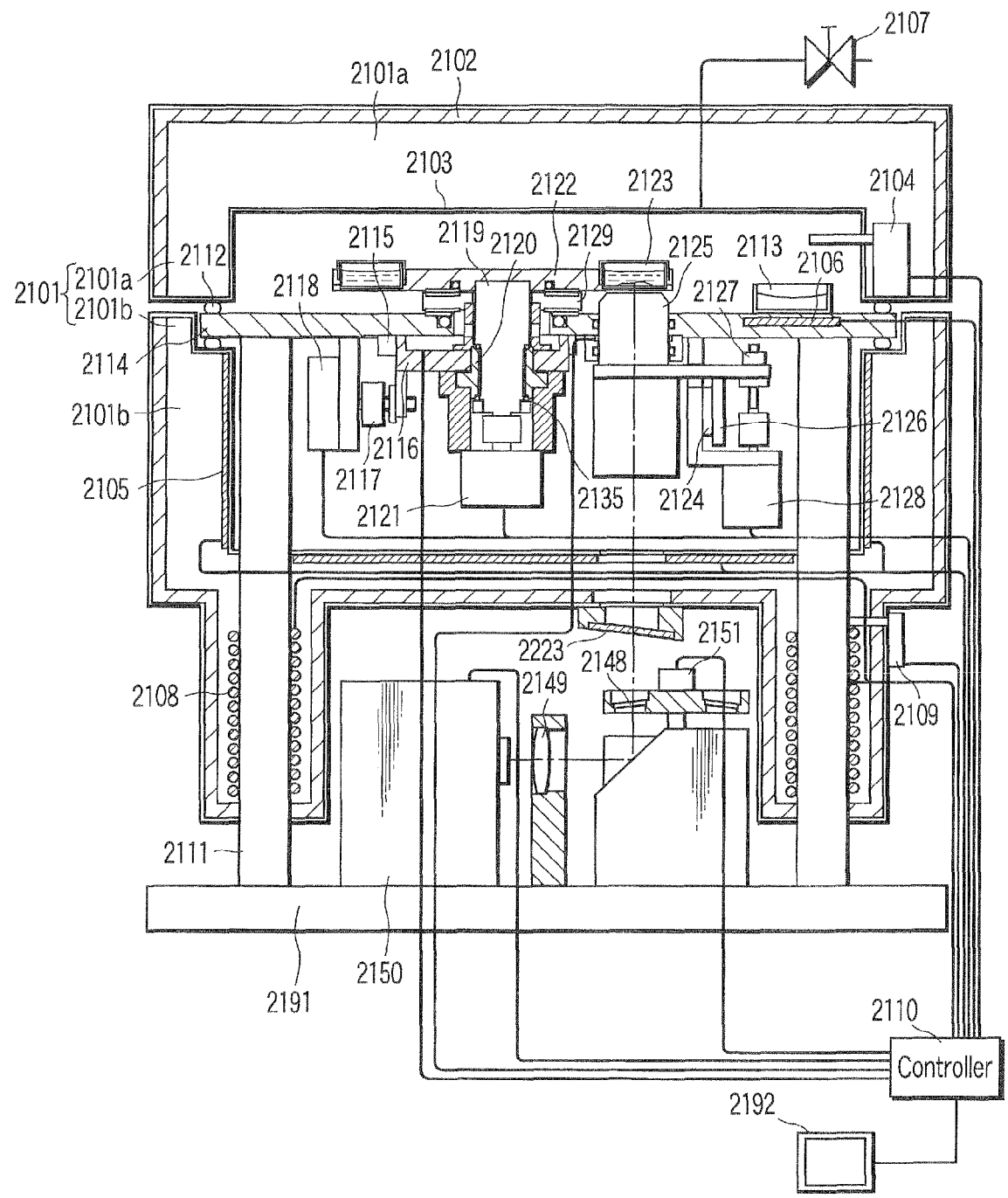
FIG. 8 schematically shows a culture microscope apparatus of a fifth embodiment of the present invention.

FIG. 8 schematically shows the culture microscope apparatus of a fifth embodiment of the present invention. The culture microscope apparatus basically comprises a microscope device to observe cultured cells and a culture device 2101 capable of controlling temperature, humidity and carbon dioxide gas concentration so that they have values suitable for the cultured cells.

[Outline of Microscope Device]

In FIG. 8, the microscope device comprises an objective lens 2125, which allows of observation of the cultured cells in a specimen 2123 (i.e., culture case containing the cultured cells), an image pickup device 2150, which picks up an image of the cultured cells enlarged by the objective lens 2125, a moving device, which relatively moves the specimen 2123 (i.e., the cultured cells) and the objective lens 2125, an upper base member 2114 on which the objective lens 2125 and the moving device are placed, a lower base member 2191 on which the image pickup device 2150 is placed, and support columns 2111 coupling the upper base member 2114 to the lower base member 2191.

The upper base member 2114, the lower base member 2191 and the support columns 2111 are all made of a low expansion material with a little expansion due to heat.

The moving device comprises a straight moving guide 2115, a horizontally moving member 2116, a ball screw 2117, a stepping motor 2118, a rotation shaft 2119, a rotation shaft bearing 2120, a stepping motor 2121, a table 2122, a straight moving guide 2124, a vertically moving member 2126, a ball screw 2127 and a stepping motor 2128.

The straight moving guide 2115, the horizontally moving member 2116, the ball screw 2117 and the stepping motor 2118 are all provided under the upper base member 2114. The straight moving guide 2115 supports the horizontally moving member 2116 movably in one direction, and the stepping motor 2118 moves the horizontally moving member 2116 through the ball screw 2117. The horizontally moving member 2116 holds the rotation shaft bearing 2120 and the stepping motor 2121. The stepping motor 2121 is located coaxially with the rotation shaft bearing 2120. The rotation shaft bearing 2120 supports the rotation shaft 2119 rotatably vertically to a horizontal plane and pressurizes the rotation shaft 2119. Balls 2135 are provided between the rotation shaft 2119 and the rotation shaft bearing 2120 to reduce friction (see FIG. 9). A lower end of the rotation shaft 2119 is connected to the stepping motor 2121. An upper end of the rotation shaft 2119 protrudes from an upper surface of the upper base member 2114 through an opening formed in the upper base member 2114. The table 2122 on which the specimen 2123 is mounted is fixed detachably by screws to the upper end of the rotation shaft 2119.

The objective lens 2125 is located on a straight line extending from the rotation shaft 2119 in a moving direction of the horizontally moving member 2116. The objective lens 2125 is supported by the vertically moving member 2126. The vertically moving member 2126 is supported so that it can be moved vertically by the straight moving guide 2124 fixed to the upper base member 2114. Further, the vertically moving member 2126 is coupled to, through the ball screw 2127, the stepping motor 2128 fixed to the upper base member 2114, and moved vertically by the stepping motor 2128. The straight moving guide 2124, the vertically moving member 2126, the ball screw 2127 and the stepping motor 2128 are all provided under the upper base member 2114.

The moving device thus configured enables the relative movement of the specimen 2123 mounted on the table 2122 and the objective lens 2125. That is, the horizontally moving member 2116 can move linearly in one direction in the horizontal plane relative to the upper base member 2114. Further, the table 2122 can make rocking movement with respect to the horizontally moving member 2116. Moreover, the vertically moving member 2126 can move linearly in a vertical direction with respect to the upper base member 2114. That is, the specimen 2123 can move linearly in one direction and rock with respect to the objective lens 2125, and the objective lens 2125 can move relatively in a vertical direction with respect to the specimen 2123. As a result, the specimens 2123 can be observed. Moreover, because the image pickup device 2150 is located outside the culture device 2101, noise resulting from the temperature of the image pickup device 2150 can be reduced. Further, the upper base member 2114 and the lower base member 2191 that have different temperatures inside and outside the culture device 2101 are made of the low expansion material, such that distortion due to thermal expansion can be reduced and the adjustment of the optical system is not disturbed.

[Outline of Culture Device]

The culture device 2101 comprises the upper base member 2114, a door 2101*a* located above the upper base member 2114, and a base portion 2101*b* located under the upper base member 2114. The door 2101*a* can open and close with respect to the upper base member 2114 to mount the specimen 2123 on the table 2122. When the door 2101*a* is closed, the upper base member 2114 and the door 2101*a* define a culture space. In order to keep an airtight state between the door 2101*a* and the upper base member 2114 when the door 2101*a* is closed, an elastic seal member 2112 is provided between the door 2101*a* and the upper base member 2114. The base portion 2101*b* is held by the support columns 2111, and the elastic seal member 2112 is provided between the base portion 2101*b* and the upper base member 2114 to keep an airtight state between the base portion 2101*b* and the upper base member 2114.

The culture device 2101 comprises an insulating material 2102, a metallic interior portion 2103 made of stainless steel having antibacterial and corrosion resistance properties or anti-bacterially coated, a sensor 2104 to sense the temperature, humidity and PH in the culture device, a heater 2105 provided in the interior of the culture device for internal temperature adjustment, humidification means or a humidification heater 2106 provided on the upper base member 2114 for temperature adjustment in the culture device, an electromagnetic valve 2107 that is connected to a carbon dioxide gas cylinder to adjust the carbon dioxide gas concentration for PH adjustment and that supplies carbon dioxide gas, a column heater 2108 to adjust the temperature of the support columns 2111 coupling the inside and outside of the culture device 2101, and a support column sensor 2109 to measure the temperature of the support columns 2111. On the upper base member 2114, a humidification pad 2113 containing water for humidification in the culture device 2101 is placed at a position above the humidification heater 2106. The culture device 2101 further comprises a controller 2110 to perform an operation for maintenance of a set condition in accordance with a signal from the sensor 2104 in order to control the heater 2105, the humidification heater 2106 and the electromagnetic valve 2107.

According to such a configuration, the insulating material 2102 thermally isolates the image pickup device 2150 from the culture device 2101. The insulating material 2102 and the seal member 2112 reduce heat going in and out of the culture device 2101. This reduces the influence of outdoor air temperature changes and enables the stabilization of temperature. Moreover, as the less heat goes in and out, the capacity of the heater 2105 and the humidification heater 2106 and water capacity of the humidification pad 2113 can be reduced. Further, as plenty of nutrients are provided to the culture medium where the cells are cultured, microorganisms having high reproduction ability infiltrating therein cause an adverse effect to the cultured cells. However, the interior portion 2103 of the culture device 2101 having the antibacterial and corrosion resistance properties prevents the infiltration of the microorganisms and can maintain the activity of the cultured cells.

Furthermore, high humidity is maintained in the culture space of the culture device 2101 to prevent the culture medium from being dried due to the evaporation of water. Therefore, if the specimen operated at a room temperature of about 23° C. is brought into the culture device, condensation is caused on the outside of the container, resulting in the deterioration of the observation image through the microscope. It is thus preferable that humidification control described below is performed for the culture device 2101. The culture device 2101 has a door sensor, which is not specifically shown, to sense that the door 2101*a* is opened or closed. In accordance with a signal (an instruction to mount the specimen 2123) from the door sensor, the controller 2110 causes the humidification heater 2106 to warm the humidification pad 2113 to start humidification after a certain period of time has passed (e.g., after ten minutes) so that the cultured cells including the container (i.e., the specimen 2123) will be at the same temperature as that inside the culture device 2101. Owing to this control, the cultured cells are humidified after reaching the same temperature as that inside the culture device 2101, whereby a satisfactory microscope observation image can be obtained without causing condensation in the cultured cells including the container. Moreover, if a specimen mounting button is provided in the controller 2110 instead of the door sensor and the controller 2110 performs similar humidification control in accordance with an instruction based on the specimen mounting button, similar effects can be provided. In addition, instead of turning the humidification heater 2106 on and off, a door provided for the humidification pad 2113 may be opened and closed.

[Details of Table Section and Objective Lens Section of Microscope Device]

Figure 9:
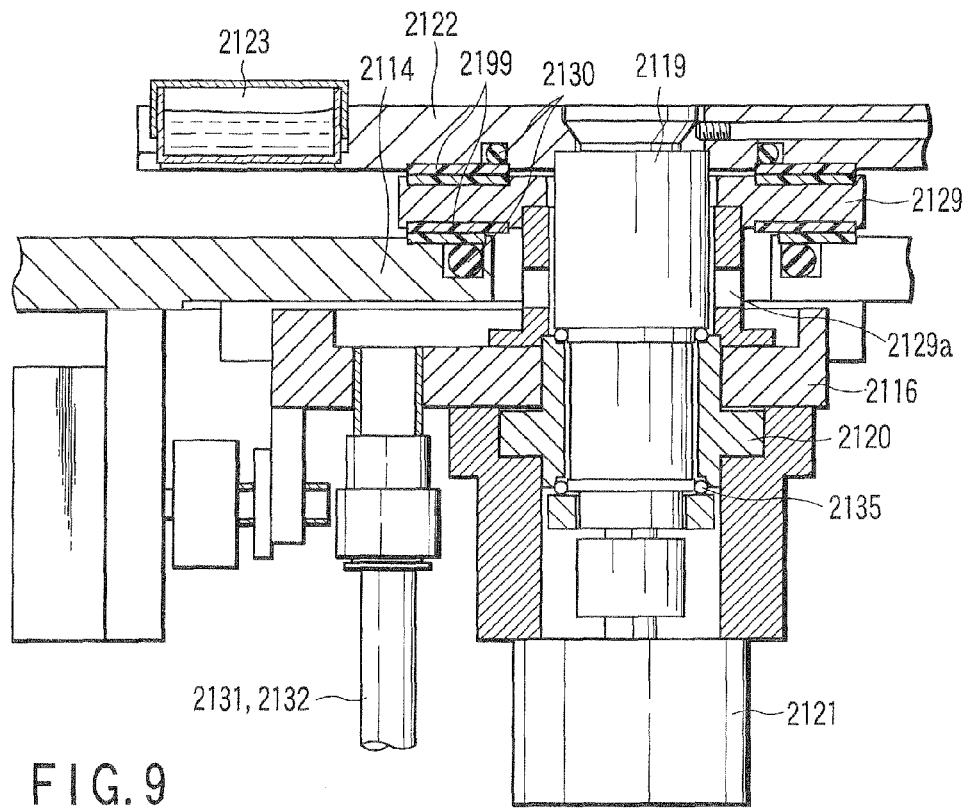
FIG. 9 shows in an enlarged manner a peripheral part of a table shown in FIG. 8.

FIG. 9 shows in an enlarged manner a peripheral part of the table shown in FIG. 8. Between the table 2122 and the upper base member 2114, an intermediate member 2129 is located fixedly to the horizontally moving member 2116. Between the table 2122 and the intermediate member 2129, there are provided two ring-shaped seat seals 2199 made of ethylene tetrafluoride (PFTE), and an elastic O-ring 2130. The O-ring 2130 is located in a pressed state. Also, between the upper base member 2114 and the intermediate member 2129, there are provided the two seat seals 2199 and the O-ring 2130, and the O-ring 2130 is located in a pressed state.

Figure 10:
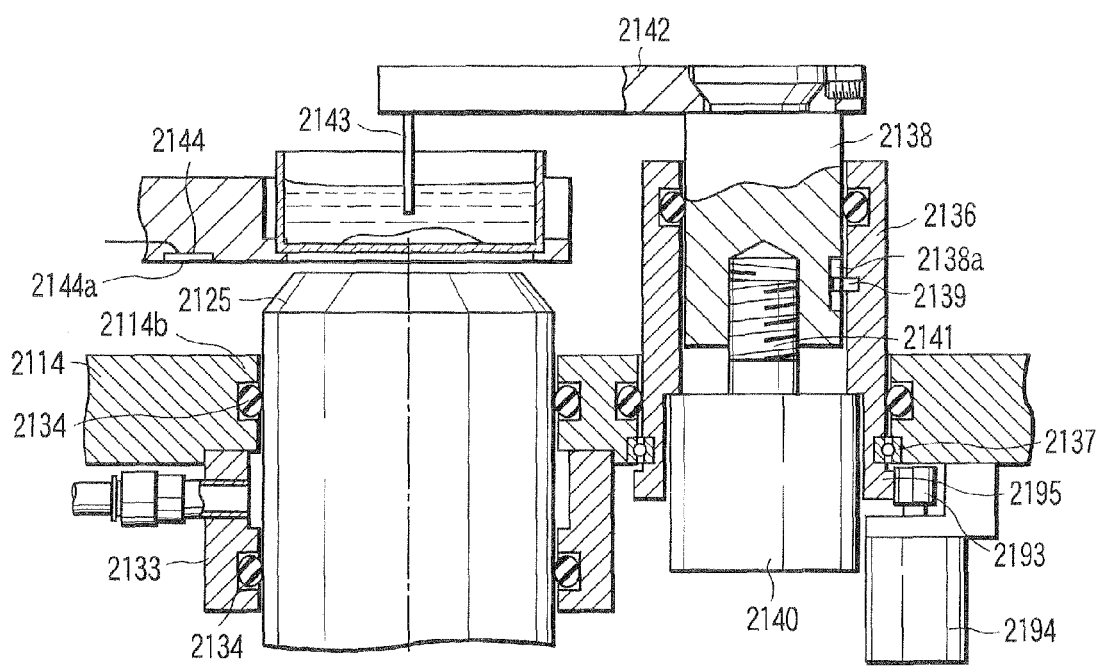
FIG. 10 shows in an enlarged manner a peripheral part of an objective lens shown in FIG. 8.

FIG. 10 shows in an enlarged manner a peripheral part of the objective lens shown in FIG. 8. The upper base member 2114 has an opening 2114*b* to protrude the objective lens 2125, and a groove is formed on an inner peripheral surface of the opening 2114*b*, and an elastic O-ring 2134 is received in the groove of the opening 2114*b*. In such a state that the objective lens 2125 protrudes out of an upper surface of the upper base member 2114 through the opening 2114*b*, the O-ring 2134 is pressed.

In FIG. 9, the rotation of the stepping motor 2121 rocks the table 2122. The table 2122 rocks such that sliding is mainly caused between the two seat seals 2199 of the PFTE material having a low friction coefficient. Even if a distance change is caused between the table 2122 and the intermediate member 2129 through the seat seals 2199, the O-ring 2130 elastically deforms to absorb the distance change to always prevent gap formation. Similarly, even if a distance change is caused between the upper base member 2114 and the intermediate member 2129 through the seat seals 2199, the O-ring 2130 works similarly to prevent the gap formation. Moreover, as the seat seals 2199 have a low friction coefficient, sliding resistance is kept low. Even if members constituting the guides and stages have lower rigidity, accurate movement is possible. Further, low frictional force can prevent the abrasion of the members.

Furthermore, in FIG. 10, a distance change is also caused between the objective lens 2125 and the opening 2114*b* of the upper base member 2114 in the vertical movement of the objective lens 2125, but the O-ring 2134 elastically deforms to absorb the distance change to always prevent gap formation.

In FIG. 8, if the door 2101*a* is closed, the seal member 2112 is pressed between the door 2101*a* and the upper base member 2114. Therefore, no gap is formed between the door 2101*a*, that is, the culture device 2101 and the upper base member 2114.

Thus, the microscope device is isolated from the moisture of the culture device 2101 by the upper base member 2114, the base portion 2101*b* and sealing structures (the seal member 2112, the seat seals 2199, the O-ring 2130 and the O-ring 2134). In other words, the upper base member 2114, the base portion 2101*b* and the sealing structures (the seal member 2112, the seat seals 2199, the O-ring 2130 and the O-ring 2134) constitute isolation means or an isolator to isolate the microscope device from the moisture of the culture device 2101.

This configuration can keep the culture space defined by the closed door 2101*a* and the upper base member 2114 from the outside air. Further, the table 2122 and the objective lens 2125 inside the culture space can be moved from the outside of the culture space. It is thus easy to maintain the temperature and humidity of the culture space, so that necessary heater capacity and a necessary amount of water can be reduced. It is further possible to reduce the infiltration of moisture into a mechanism part (the moving device) and an optical part, enabling the prevention of rust and condensation.

Furthermore, the use of PTFE having a low friction coefficient for a sealing surface enables a microscope having both positional accuracy and sealing performance.

Even with the above-described sealing structures (the seal member 2112, the seat seals 2199, the O-ring 2130 and the O-ring 2134), moisture slightly infiltrates into a lower surface side of the upper base member 2114. In order not to expose the mechanism part (the moving device) and the optical part to such moisture, in FIG. 9, the gap between the lower surface of the upper base member 2114 and the horizontally moving member 2116 is set at 0.1 mm or less, and an intake pipe 2131 and an exhaust pipe 2132 are connected to the horizontally moving member 2116. The intake pipe 2131 and the exhaust pipe 2132 are led to the external, and an air pressure source is connected to the intake pipe 2131 for air intake. The intake pipe 2131 is wound several times in the culture device 2101 to elongate a passage in the culture device 2101. The intake pipe 2131 and the exhaust pipe 2132 constitute dehumidifying means or a dehumidifier that connects the atmosphere in the microscope device to the air outside the culture microscope apparatus and that dehumidifies the atmosphere in the microscope device. Further, the intermediate member 2129 comprises, at a cylindrical portion connected to the horizontally moving member 2116, a communication hole 2129a penetrating the cylindrical portion.

In FIG. 10, the upper base member 2114 is provided with a capturing member 2133 extending from the upper base member 2114 in the axial direction of the objective lens 2125. The capturing member 2133 has an opening through which the objective lens 2125 passes, and the O-ring 2134 is mounted in the groove formed in the inner peripheral surface of the opening to press the objective lens 2125. The above-mentioned intake pipe 2131 and the exhaust pipe 2132 are also connected between the O-ring 2134 of the capturing member 2133 and the O-ring 2134 of the upper base member 2114.

The moisture that has infiltrated from the culture space defined by the closed door 2101a and the upper base member 2114 through the space between the two seat seals 2199 diffuses between the upper base member 2114 and the horizontally moving member 2116 from a gap between the intermediate member 2129 and the rotation shaft 2119 through the communication hole 2129a. The moisture diffused between the upper base member 2114 and the horizontally moving member 2116 is discharged to the outside from the exhaust pipe 2132 together with the outside air introduced from the intake pipe 2131. The outside air introduced from the intake pipe is warmed by the long passage in the culture device 2101 and reaches the horizontally moving member 2116 without dropping the temperature of the members. The moisture that has infiltrated from the space between the objective lens 2125 and the O-ring 2134 is similarly discharged to the outside.

The configuration described above also forces the slight amount of moisture that has infiltrated from each of the sealing structures (the seat seals 2199, the O-ring 2130 and the O-ring 2134) to be discharged to the outside. Thus, moisture does not reach the mechanism part (the moving device) and the optical part without the fear of rust and condensation. Further, a constant temperature of the objective lens 2125 can eliminate focal movement of the objective lens 2125 due to temperature changes. This enables a long-term observation without defocusing.

[Manipulator]

Next, a manipulator to introduce genes and drugs into the cultured cells will be described referring to FIG. 10. The manipulator has an arm 2142 capable of rocking and vertical movement, and the arm 2142 holds a syringe 2143 at an end. The arm 2142 is detachably fixed to a vertically moving shaft 2138 by screws. The vertically moving shaft 2138 is received in a cylindrical rotation shaft 2136 and can move vertically with respect to the rotation shaft 2136. The rotation shaft 2136 is attached to the upper base member 2114 through a bearing 2137 and can rotate with respect to the upper base member 2114. The rotation shaft 2136 comprises a main wheel 2195 at a lower end. The main wheel 2195 engages with a pinion 2193 attached to an output shaft of a stepping motor 2194 fixed to the upper base member 2114. The vertically moving shaft 2138 has a female screw at a lower end. The female screw of the vertically moving shaft 2138 engages with a male screw formed in the output shaft of a stepping motor 2140. The vertically moving shaft 2138 has a groove 2138a extending vertically in an outer peripheral surface. A pin 2139 fixed to the rotation shaft 2136 is received in the groove 2138a. The pin 2139 determines the range of vertical movement of the vertically moving shaft 2138 with respect to the rotation shaft 2136, and regulates the rotation of the vertically moving shaft 2138 with respect to the rotation shaft 2136. A position to fix the arm 2142 to the vertically moving shaft 2138 is adjusted so that the distance between the syringe 2143 and a core of the rotation shaft 2136 will be the same as the distance between an optical axis of the objective lens 2125 and the core of the rotation shaft 2136.

In the configuration described above, the arm 2142 can be moved to locate the syringe 2143 at the cells in the center of viewing field even in a highly humid environment, and for example, a reagent placed on the upper base member 2114 can be administered to the cultured cells. Further, the stepping motor 2194 to rotate the arm 2142 and the stepping motor 2118 to horizontally move the specimen 2123 can be driven in conjunction with each other to locate the syringe 2143 at an optional position in a predetermined range.

In the culture microscope apparatus of the present embodiment, when the table 2122 and the arm 2142 are removed, the only members protruding on the upper side of the upper base member 2114 are cylindrical members (the rotation shaft 2119 and the intermediate member 2129 of the moving device, the rotation shaft 2136 of the manipulator), so that cleaning can be easily performed.

[Water Supply]

A water supply device for a water-immersion objective lens will be described referring to FIG. 10. The culture microscope apparatus of the present embodiment comprises the water supply device, which supplies water to the water-immersion objective lens, considering the case where the objective lens 2125 is a water-immersion objective lens. The water supply device comprises a cooler capable of setting a temperature different from a set temperature of the culture device 2101. The cooler comprises, but not limited to, a peltier element 2144 in the present embodiment. On a lower surface of the table 2122, the peltier element 2144 is fixed at a place where it can be located on the optical axis of the objective lens 2125 when the table 2122 moves. The peltier element 2144 has a water supply surface 2144a that can face the objective lens 2125. The culture space is maintained in a saturated state close to a relative humidity of 100%, so that if the water supply surface 2144a of the peltier element 2144 is cooled off several times, steam is condensed on the water supply surface 2144a. The table 2122 is moved by the above-mentioned moving device to locate the water supply surface 2144a above the objective lens 2125 and then the table 2122 is lowered such that water condensed on the water supply surface 2144a can be supplied to the objective lens 2125. According to this configuration, water can be supplied to the objective lens 2125 only by the peltier element 2144 without using an extra member. Thus, an inexpensive water supply device can be provided.

The peltier element 2144 can be provided not on the table 2122 but on the upper surface of the upper base member 2114, and the above-mentioned manipulator can be used to supply water condensed on the upper surface of the peltier element 2144 to the objective lens 2125. This configuration can reduce the temperature changes of the specimen because the peltier element 2144 is not provided on the table 2122.

[Dark Field]

The microscope device is capable of fluorescent observation and dark field observation. The fluorescent observation is used to identify the expression of fluorescent protein at a target part, and the dark field observation is used to visualize the nucleus and outline of cells for confirmation of the positions of cells, the state of culture or bacterial contamination.

Figure 11:
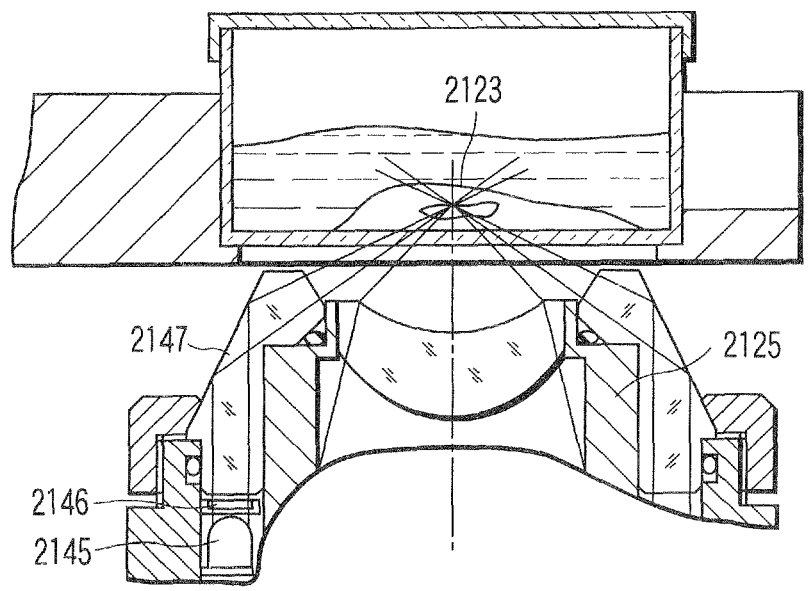
FIG. 11 shows an illumination device applicable to a microscope device shown in FIG. 8.

The microscope device includes an illumination device for illuminating the cultured cells and an observation device to observe the cultured cells. FIG. 11 shows the illumination device applicable to the microscope device shown in FIG. 8. As shown in FIG. 11, the illumination device comprises light emitting diodes 2145 having different emission wavelengths, excitation filters 2146 located in front of the light emitting diodes 2145, and a bending member 2147. The light emitting diodes 2145, the excitation filters 2146 and the bending member 2147 are all located at an outer peripheral part of the objective lens 2125. The excitation filters 2146 selectively transmit light having a specific wavelength among wavelengths of illumination light emitted from the light emitting diodes 2145. The bending member 2147 bends the illumination light that has penetrated the excitation filters 2146 and orients it toward the specimen 2123.

As shown in FIG. 8, the observation device comprises the objective lens 2125, an image-forming lens 2149, which cooperates with the objective lens 2125 to constitute an image-forming optical system, the image pickup device 2150, which picks up an optical image formed by the image-forming optical system, and a monitor 2192 to display the image obtained by the image pickup device 2150. The base portion 2101b is provided with an optical window 2223 so that light from the specimen 2123 travels to the image pickup device 2150 through the objective lens 2125 and the image-forming lens 2149. The optical window 2223 may comprise a transparent optical member such as glass plate. The observation device further comprises an emission filter 2148, which selectively transmits light having a specific wavelength among wavelengths of observation light directed to the image pickup device 2150, and a turret 2151 to locate the emission filter 2148 on the optical axis as required. The image pickup device 2150 is preferably a cooled CCD considering the fluorescent observation.

In the dark field observation, in FIG. 8, the turret 2151 is switched to locate an air hole on the optical axis and displace the emission filter 2148 from the optical axis. In FIG. 11, the light emitted by the light emitting diodes 2145 penetrates the excitation filters 2146, and illuminates the specimen 2123 due to the bending member 2147 from the outside of NA of the objective lens 2125. Therefore, the illumination light and the light regularly reflected by the lower surface of the specimen container are not captured by the objective lens 2125. The reflected light and scattered light alone due to the cultured cells in the specimen 2123 are captured by the objective lens 2125 and detected by the image pickup device 2150. Thus, even transparent cultured cells can be visualized without being dyed. Further, because a generally used transmitted-light illumination portion used in phase difference observation is not necessary, a space is produced above the specimen, thus facilitating operations including taking the specimen 2123 in and out of the culture device 2101 and administering the reagent to the specimen 2123.

Figure 12:
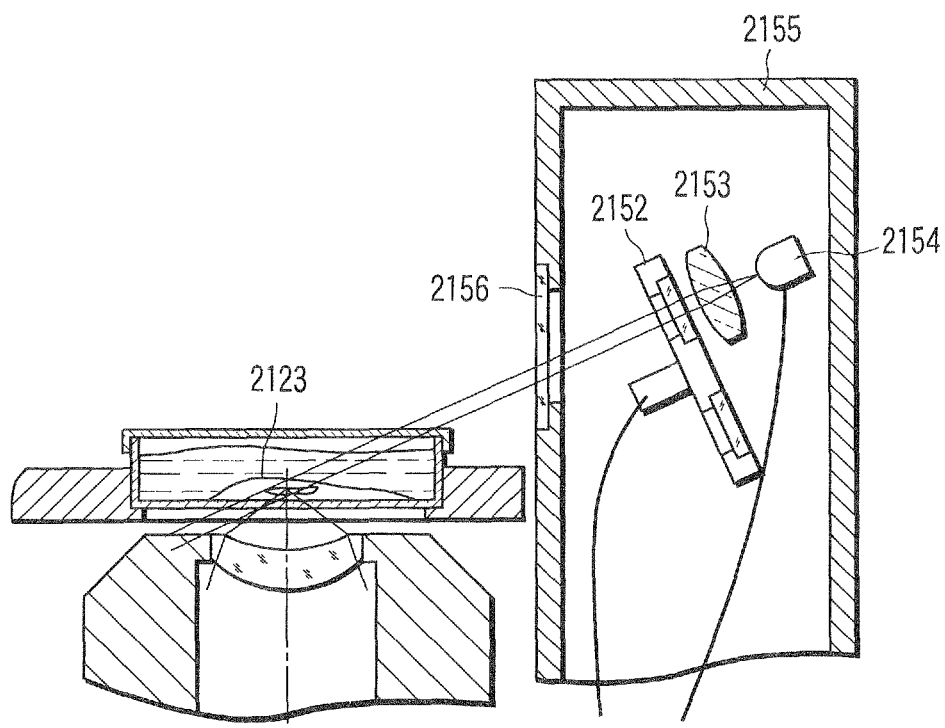
FIG. 12 shows another illumination device applicable to the microscope device shown in FIG. 8.

FIG. 12 shows another illumination device applicable to the microscope device shown in FIG. 8. If NA of the objective lens 2125 is, for example, 0.85, the range of light captured by the objective lens 2125 will be about 60 degrees from the optical axis. Illumination optical axes are set on a bus at 70 degrees from the optical axis toward the center of a specimen container bottom surface, and an excitation filter 2152, a collimating lens 2153 and a light emitting diode 2154 are located on the illumination optical axes. The excitation filter 2152, the collimating lens 2153 and the light emitting diode 2154 are sealed by a dustproof glass 2156 inside an illumination member 2155 provided out of a moving range of the table 2122 on the upper base member 2114.

In other words, the illumination device of FIG. 12 comprises the light emitting diode 2154 to emit the illumination light, the collimating lens 2153 to form the illumination light emitted by the light emitting diode 2154 into parallel light, the excitation filter 2152, which selectively transmits light having a specific wavelength among wavelengths of the illumination light emitted from the light emitting diode 2154, the illumination member 2155 housing the light emitting diode 2154, the collimating lens 2153 and the excitation filter 2152, and the dustproof glass 2156 constituting an optical window provided in the illumination member 2155. The illumination optical axis passing the light emitting diode 2154, the collimating lens 2153 and the excitation filter 2152 is inclined at 70 degrees with respect to the optical axis of the objective lens 2125.

The light emitted by the light emitting diode 2154 is brought into parallel light by the collimating lens 2153, and illuminates uniformly within an observation field in the objective lens 2125. The light that has penetrated the specimen 2123 is the light outside the NA of the objective lens 2125, and is therefore not captured by the objective lens 2125. The reflected light and scattered light alone due to the specimen 2123 are captured by the objective lens 2125 and detected by the image pickup device 2150. Therefore, effects similar to those in dark field illumination by the illumination device shown in FIG. 11 are provided; for example, even transparent cultured cells can be visualized without being dyed, and the transmitted-light illumination portion is not necessary. When the fluorescent observation is not performed together or when narrow-band wavelengths are not necessary in an excitation wavelength, the excitation filter 2152 may be removed from the configuration.

[Fluorescence]

The fluorescent observation can also be performed using the illumination device in FIG. 11. In the fluorescent observation, in FIG. 8, the turret 2151 is switched to locate on the optical axis the emission filter 2148 adapted to a fluorescent wavelength of the specimen 2123. In FIG. 11, light having a wavelength that is needed to excite the specimen among wavelengths of light emitted from the light emitting diode 2154 is selectively transmitted by the excitation filter 2146 and illuminates the specimen 2123. The specimen 2123 excited by the illumination light emits fluorescence light having a wavelength longer than the wavelength used for the excitation. The fluorescence light is captured by the objective lens 2125, brought into parallel light and exits from the objective lens 2125 to reach the emission filter 2148. The light that has penetrated the emission filter 2148 is imaged on a light receiving surface of the image pickup device 2150 by the image-forming lens 2149, and displays an object image on the monitor 2192. Owing to the dark field observation, the illumination light is not captured by the objective lens 2125, so that SN in accordance with auto-fluorescence in the objective lens 2125 is not reduced by the illumination light.

The fluorescent observation can also be performed using the illumination device in FIG. 12. In FIG. 12, the light emitted by the light emitting diode 2154 is brought into parallel light by the collimating lens 2153, and the light needed to excite the specimen is selectively transmitted by the excitation filter 2152 and illuminates the specimen uniformly. The function leading to the image-forming is the same as in the illumination device in FIG. 11.

Furthermore, instead of the light emitting diode 2154, a light source provided outside the apparatus may be used in such a manner to transmit through a fiber. When the fiber is used, a high luminance light source can be used because it is not necessary to consider the intensity of light and heat of the light source.

Here, the illumination device for the fluorescent observation is an oblique illumination device as shown in FIG. 11 and FIG. 12, but it may also be an incident-light illumination device. That is, the illumination device for the fluorescent observation includes the objective lens 2125 and may have the configuration similar to those of the illumination devices described in the first embodiment to fourth embodiment.

[Phase Difference]

Figure 13:
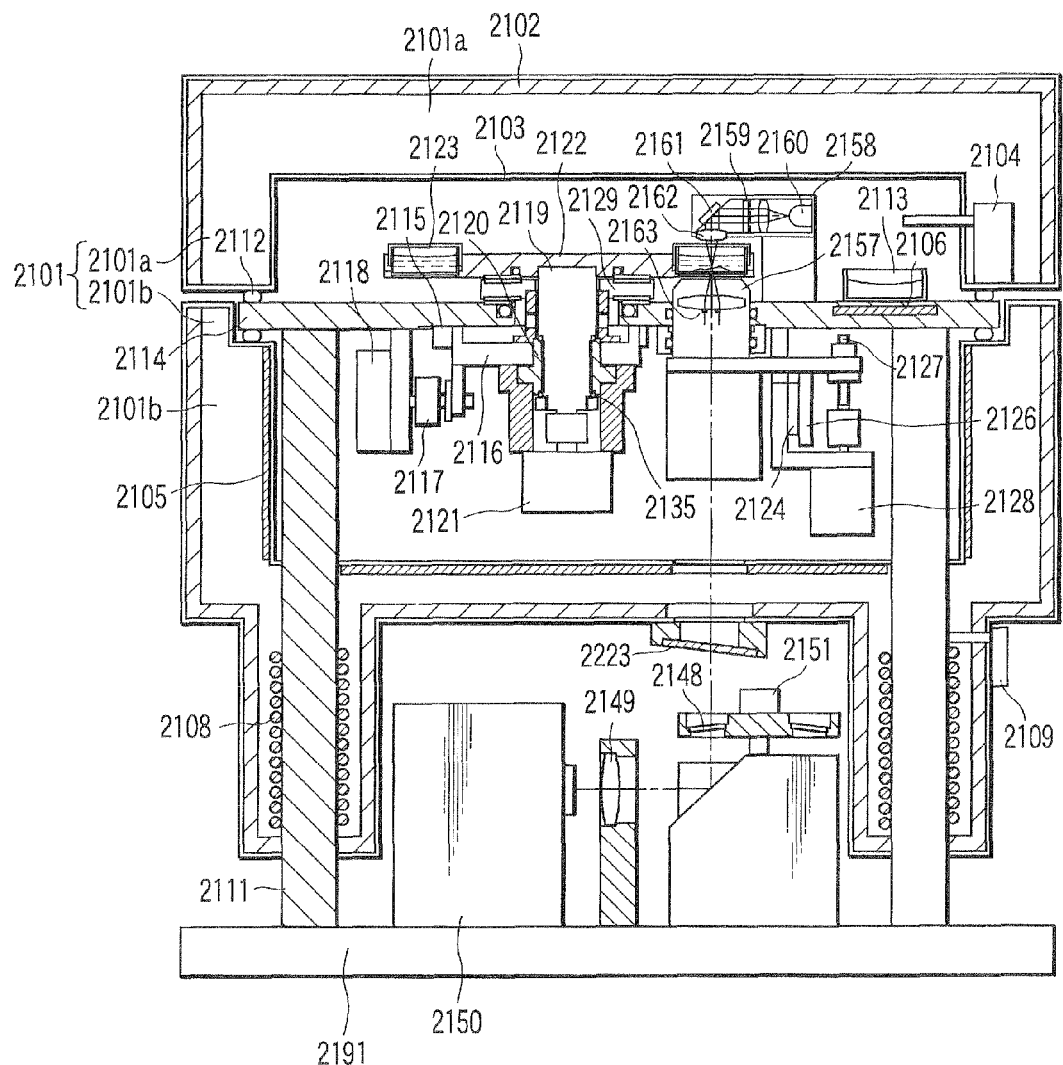
FIG. 13 shows a modification of the culture microscope apparatus of the fifth embodiment of the present invention.
Figure 14:
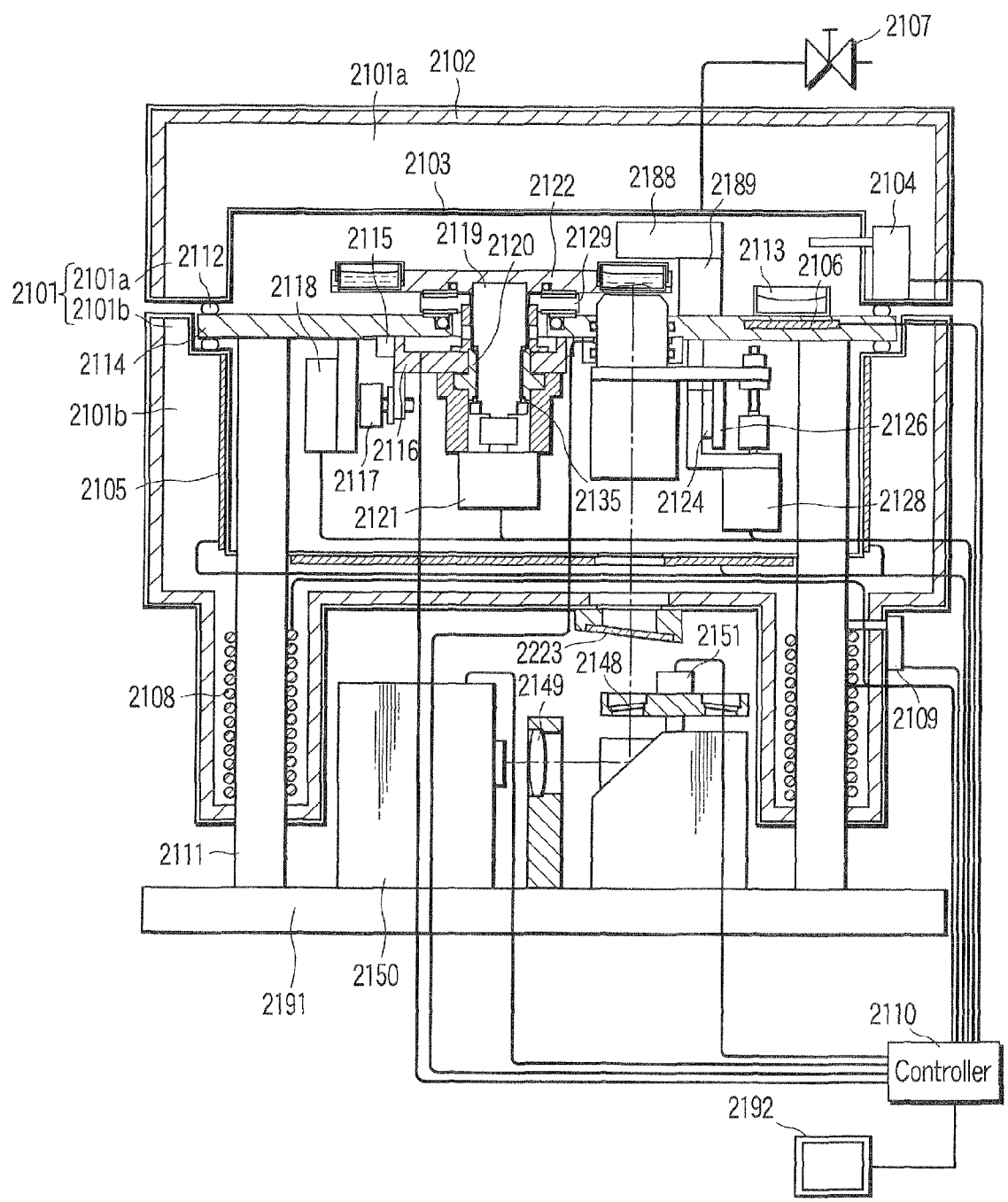
FIG. 14 shows another modification of the culture microscope apparatus of the fifth embodiment of the present invention.

FIG. 13 shows a modification of the culture microscope apparatus of the present embodiment. More specifically, the culture microscope apparatus that has changed the microscope device shown in FIG. 8 from the configuration suitable for the dark field observation to the configuration suitable for the phase difference observation is shown. In FIG. 13, members indicated by the same numerals as the members shown in FIG. 8 are the same and will not be described in detail.

In the culture microscope apparatus of the present modification, the microscope device comprises a phase difference objective lens 2157 in place of the objective lens 2125 in FIG. 8 and also comprises a transmitted-light illumination device in place of the dark field illumination device in FIG. 11 and FIG. 12, as understood from FIG. 13.

The transmitted-light illumination device comprises an illumination support column 2158, a ring slit 2159, a light emitting diode 2160, a reflecting mirror 2161 and a collimating lens 2162. The illumination support column 2158 is placed out of the moving range of the table 2122 on the upper base member 2114. The illumination support column 2158 houses the ring slit 2159, the light emitting diode 2160 and the reflecting mirror 2161. The collimating lens 2162 is inserted into an opening of the illumination support column 2158 and closely fixed by an adhesive material. The ring slit 2159 has a ring-shaped opening and is located at a position conjugate with a rear focal plane of the phase difference objective lens 2157. The light emitting diode 2160 is located in the vicinity of the ring slit 2159.

The phase difference objective lens 2157 comprises a phase plate 2163 on the rear focal plane. The size of the phase plate 2163 includes the projected ring slit 2159. That is, an image of the ring slit 2159 is projected on an inner side of the phase plate 2163. Moreover, the phase plate 2163 comprises an optical member that shifts the phase of transmitted light by ¼ wavelengths, and an ND film that attenuates the transmitted light.

Light emitted from the light emitting diode 2160 passes through the opening of the ring slit 2159, has its direction changed by the reflecting mirror 2161, is brought into parallel light by the collimating lens 2162, and illuminates the specimen 2123 uniformly.

Zero-th light that has penetrated the specimen 2123 converges on the phase plate 2163 of the phase difference objective lens 2157, and is subjected to phase shift and light amount attenuation. Further, primary light diffracted at the specimen 2123 does not converge on the phase plate 2163 on the rear focal plane of the phase difference objective lens 2157, and is not therefore subjected to phase shift and light amount attenuation.

The zero-th light and the primary light are imaged on a light receiving surface of the image pickup device 2150 by the image-forming lens 2149. The phase shift of the zero-th light performed by the phase plate 2163 causes interference between the zero-th light and the primary light, so that even undyed specimens can be observed. Moreover, the collimating lens 2162 shuts off the culture space from the inside of the illumination support column 2158, so that condensation is not caused on optical members inside the illumination support column.

<Another Modification of Fifth Embodiment>

Figure 15:
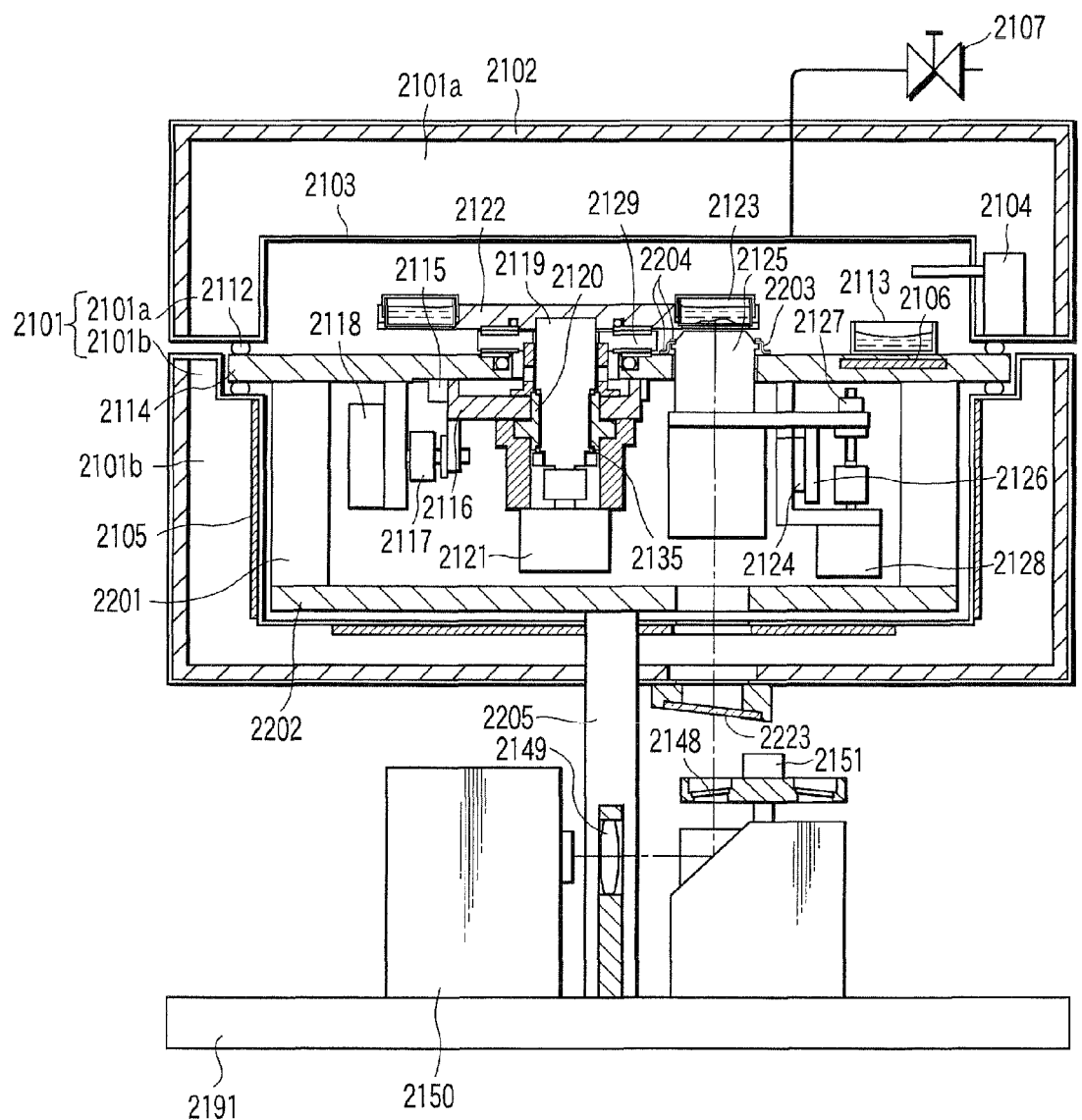
FIG. 15 shows still another modification of the culture microscope apparatus of the fifth embodiment of the present invention.

FIG. 15 shows another modification of the culture microscope apparatus of the fifth embodiment of the present invention. More specifically, the culture microscope apparatus is shown in which a dimmer unit is added to the culture microscope apparatus shown in FIG. 8. In FIG. 15, members indicated by the same numerals as the members shown in FIG. 8 are the same and will not be described in detail.

In the culture microscope apparatus of the present modification, a dimmer unit 2188 is located above the objective lens 2125. The dimmer unit 2188 faces the objective lens 2125, and the specimen 2123 to be observed is properly located between the dimmer unit 2188 and the objective lens 2125. The dimmer unit 2188 is supported by a support column 2189, and the support column 2189 is fixed to the upper base member 2114 out of the moving range of the table 2122. The dimmer unit 2188 may comprise the dimmer unit described in the first embodiment to fourth embodiment. That is, the dimmer unit 2188 has the same configuration as those of the dimmer unit 1122, the dimmer unit 1201 or the dimmer unit 1301.

According to the present modification, it is possible to significantly reduce the discoloration of the fluorescent dyes that are not targeted for observation, and to observe the fluorescent image with good contrast for a long period of time.

<Still Another Modification of Fifth Embodiment>

FIG. 15 shows still another modification of the culture microscope apparatus of the fifth embodiment of the present invention. In FIG. 15, members indicated by the same numerals as the members shown in FIG. 8 are the same and will not be described in detail.

The upper base member 2114 in the culture device 2101 is set up with a leg attachment portion 2202 fixed through support columns 2201, and the center of the leg attachment portion 2202 and the lower base member 2191 are connected by a leg portion 2205.

Furthermore, the following member is used as a seal member 2203 of the objective lens 2125. The seal member 2203 is a thin elastic rubber material, and has a cylindrical portion and two planar portions. The two planar portions are fixed to the objective lens 2125 and the upper base member 2114 through a fixing member 2204.

The leg attachment portion 2202 and the lower base member 2191 that have different temperature settings inside and outside the culture device 2101 are connected by the leg portion 2205, so that the distortion of the material caused by an expansion difference due to the temperature can be reduced and the optical adjustment is not disturbed.

Furthermore, the seal member 2203 enables sealing with a low sliding resistance, allowing an improvement in positional repeatability.

<Further Still Another Modification of Fifth Embodiment>

Figure 16:
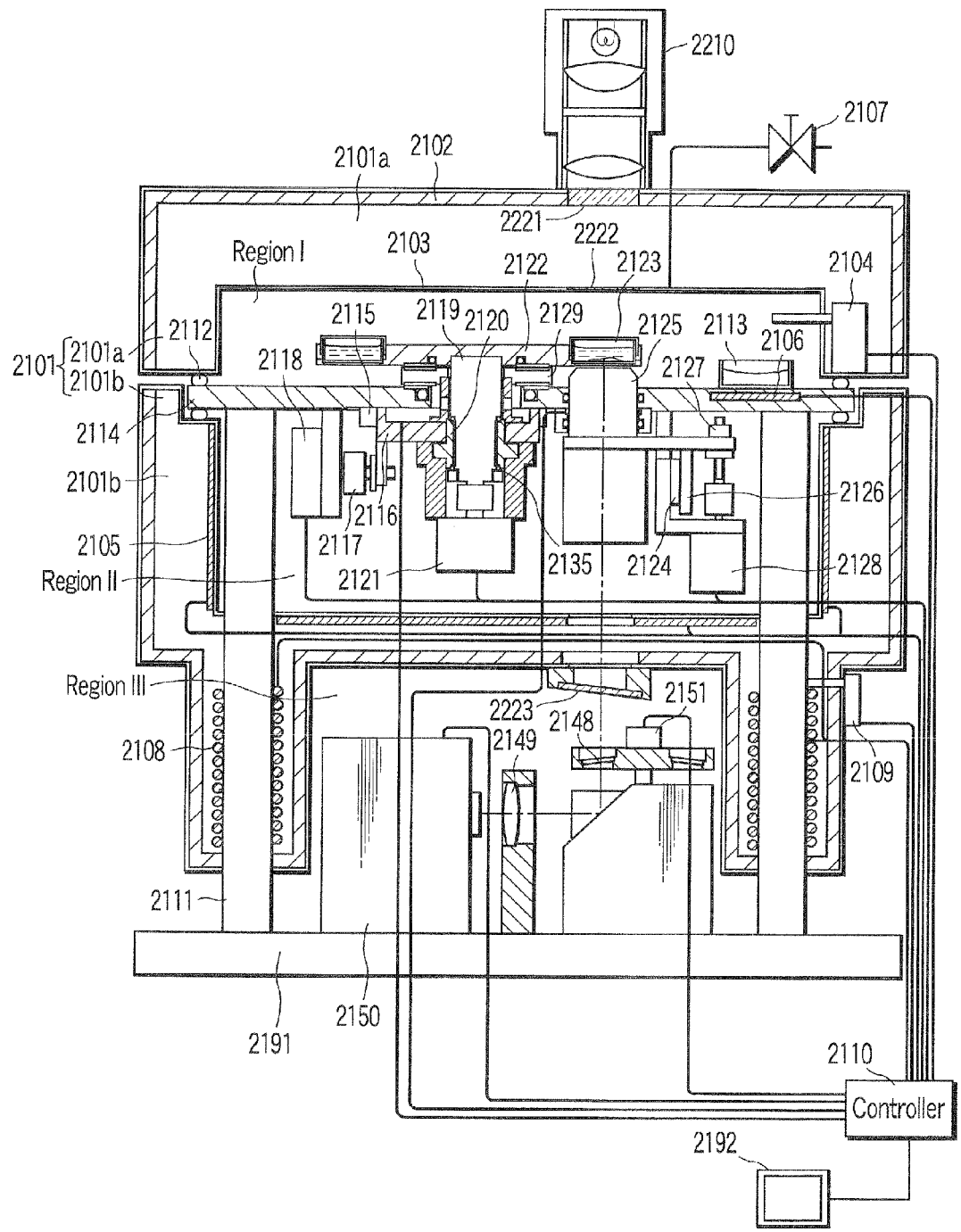
FIG. 16 shows further still another modification of the culture microscope apparatus of the fifth embodiment of the present invention.

FIG. 16 shows further still another modification of the culture microscope apparatus of the fifth embodiment of the present invention. In FIG. 16, members indicated by the same numerals as the members shown in FIG. 8 are the same and will not be described in detail.

The culture microscope apparatus of the present modification further comprises a transmitted-light illumination device 2210 for transmitted-light illumination of the specimen 2123, in addition to the construction of the culture microscope apparatus shown in FIG. 8. The transmitted-light illumination device 2210, which is located above the objective lens 2125, is attached to the door 2101a so as to be detached from the door 2101a. The door 2101a is provided with two optical windows 2221 and 2222, which transmit light from the transmitted-light illumination device 2210. The optical windows 2221 and 2222 may comprise transparent optical members such as glass plates.

The culture microscope apparatus has a region I that is basically defined by the door 2101a and the upper base member 2114, a region II that is basically defined by the base portion 2101b and the upper base member 2114, and a region III under the culture device 2101. In the region I, the temperature and humidity are maintained at a level equal to that in an environment inside a body of a human being, an animal or a plant. In the region II, the temperature is on a level equal that of the region I and the humidity maintained at a normal humidity level. In the region III, the temperature and humidity are on a normal temperature and normal humidity level.

The regions I, II and III are located along the optical axis of the image-forming optical system including the objective lens 2125, the image-forming lens 2149 and the image pickup device 2150. The specimen 2123 is located in the region I, and the image pickup device 2150 in the region III.

The regions II and III are optically connected through the optical window 2223, which is positioned between the regions II and III, so that light for the image-forming optical system, light from the specimen 2123, passes through a boundary between the regions II and III. The region I is optically connected to the transmitted-light illumination device 2210 through the optical windows 2221 and 2222, which are positioned between the region I and the transmitted-light illumination device 2210, so that light for the image-forming optical system, light from the transmitted-light illumination device 2210, passes into the region I.

The regions I and II satisfy the following conditional equations:

$$36° C. \leq t1 \leq 38° C., 90\% \leq h1 \leq 100\%$$

$$36° C. \leq t2 \leq 38° C., 50\% \leq h2 \leq 80\%$$

where t1 indicates the temperature of the region I, h1 indicates the humidity of the region I, t2 indicates the temperature of the region II, and h2 indicates the humidity of the region II.

The specimen 2123 and the objective lens 2125, which are weak in heat retaining and moisture retaining performance, are preferably separated from the normal temperature and normal humidity environment. An adverse effect (especially condensation) on the objective lens 2125 due to the culture environment is desirably reduced as much as possible. The image pickup device 2150 in the image-forming optical system, which is basically heating elements, is desirably located as far away from the culture environment as possible.

The culture microscope apparatus of the present modification has the region II as a buffer region, through which the specimen 2123 and the image pickup device 2150 are positioned and in which the objective lens 2125 is mainly located, so that the adverse effect (especially condensation) on the objective lens 2125 is effectively reduced and the culture environment is easily maintained in preferable condition.

Sixth Embodiment

The present embodiment is also directed to the culture microscope apparatus that causes a small change in the installed environment and that is easily cleaned, similarly to the fifth embodiment.

Figure 17:
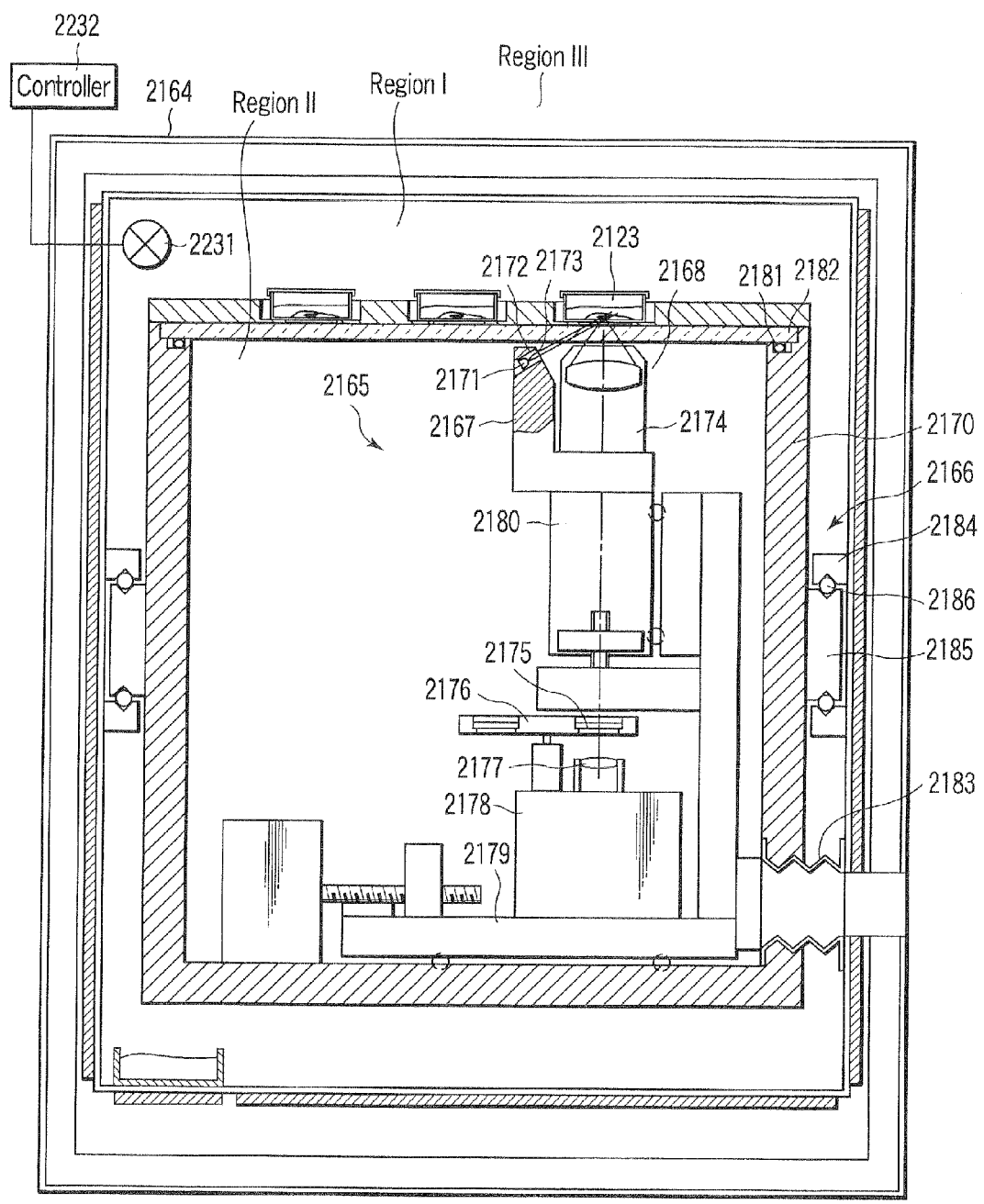
FIG. 17 schematically shows the culture microscope apparatus of a sixth embodiment of the present invention.

FIG. 17 schematically shows the culture microscope apparatus of a sixth embodiment of the present invention.

The culture microscope apparatus of the present embodiment comprises an incubator 2164 as a culture device, which can control temperature, humidity and PH and is used for the cultured cells, a microscope device 2165 housed in the incubator 2164, and a slide device 2166 that moves the microscope device 2165 between the inside and outside of the incubator 2164. The slide device 2166 is provided in the incubator 2164.

The microscope device 2165 comprises an illumination device 2167 for illuminating the cultured cells, an observation device 2168 to observe the cultured cells, a moving device 2169, and a microscope container 2170. The illumination device 2167 comprises a light emitting diode 2171, a collimating lens 2172, and an excitation filter 2173. The observation device 2168 comprises an objective lens 2174, a turret 2176 equipped with an emission filter 2175, an image-forming lens 2177, and an image pickup device 2178. The objective lens 2174 and the image pickup device 2178 constitute an image-forming optical system. The moving device relatively moves the specimen and the objective lens 2174 placed in the microscope container 2170, and comprises a horizontal stage 2179 capable of two-dimensional movement in a horizontal plane and a vertical stage 2180 placed on the horizontal stage 2179 and capable of vertical movement.

The objective lens 2174 and the illumination device 2167 are integrally fixed to the vertical stage 2180. The emission filter 2175, the turret 2176, the image-forming lens 2177 and the image pickup device 2178 are integrally fixed to the horizontal stage. The microscope container 2170 is substantially a rectangular-parallelepiped-shaped box having two openings. One opening is located on an upper surface of the microscope container 2170, while the other opening is located on a side surface of the microscope container 2170. An elastic O-ring 2181 is placed in a groove provided in the vicinity of the opening on the upper surface, and an optically transparent glass plate 2182 is fixed to the microscope container 2170 in a state pressing the O-ring 2181. The glass plate 2182 and the O-ring 2181 cooperate with the microscope container 2170 to constitute isolation means or an isolator to isolate the microscope device from the moisture of the culture device.

A communication pipe 2183 is fixed to the opening on the side surface of the microscope container 2170. The communication pipe 2183 is an extensible bellows, and connects the inside of the microscope container 2170 to the outside of the incubator 2164. The communication pipe 2183 is schematically drawn so that it extends in a direction vertical to the moving direction, that is, longitudinal direction of the microscope container 2170, that is, in the lateral direction for convenience of drawing in FIG. 17, but it is actually provided so that it extends in parallel with the moving direction, that is, longitudinal direction of the microscope container 2170. In addition, one communication pipe 2183 is drawn in FIG. 17, but two communication pipes 2183 are actually provided for air intake and exhaustion. The slide device 2166 comprises a fixed portion 2184, a moving portion 2185 and a rolling portion 2186, and the fixed portion 2184 is fixed to the incubator 2164, and the moving portion 2185 is fixed to the microscope container 2170.

The incubator 2164 is provided with a fan 2231 for the purpose of eliminating uneven temperature and humidity inside of the incubator 2164. However, vibration due to the fan 2231 deteriorates an obtained image. Therefore, the controller 2232 performs blurring prevention control to stop the fan when an image is taken. The blurring prevention control may be started simultaneously with the lighting of the illumination device 2167. This blurring prevention control makes it possible to obtain high-quality image without blurring the image due to the fan vibration.

Owing to the sealing structure using the O-ring 2181, the infiltration of moisture into the microscope container 2170 is reduced in an environment with the highly humid incubator 2164, and even a slight amount of infiltrated moisture is discharged outside by the communication pipes 2183 without causing rust and condensation in the microscope part. Moreover, the slide device 2166 is provided to make it easy to take the microscope container 2170 in and out of the incubator 2164 for easier cleaning, thereby enabling contamination prevention even in the cell culture where contamination of bacteria and molds is not preferred. Further, a slight amount of moisture infiltration is caused in a sealed portion with the O-ring, so that two communication pipes may be provided to introduce the outside air through one communication pipe and to compulsorily remove the moisture inside through the other communication pipe. This enables a more complete moisture measurement.

The culture microscope apparatus has a region I between the incubator 2164 and the microscope container 2170, a region II within the microscope container 2170, and a region III out of the incubator 2164. In the region I, the temperature and humidity are maintained at a level equal to that in an environment inside a body of a human being, an animal or a plant. In the region II, the temperature is on a level equal that of the region I and the humidity is maintained at a normal humidity level. In the region III, the temperature and humidity are on a normal temperature and normal humidity level.

The regions I, II and III are located along the optical axis of the image-forming optical system of the observation device 2168. The specimen 2123 is located in the region I.

The regions I and II are optically connected through the optically transparent glass plate 2182, which is positioned between the regions I and II, so that light for the observation device 2168, light from the specimen 2123, passes through a boundary between the regions I and II.

The regions I and II, also in the present embodiment, satisfy the following conditional equations:

$$36° C. \leq t1 \leq 38° C., 90\% \leq h1 \leq 100\%$$

$$36° C. \leq t2 \leq 38° C., 50\% \leq h2 \leq 80\%$$

where t1 indicates the temperature of the region I, h1 indicates the humidity of the region I, t2 indicates the temperature of the region II, and h2 indicates the humidity of the region II.

The culture microscope apparatus of the present embodiment has the region II, in which the observation device 2168 is located, so that the adverse effect (especially condensation) on the observation device 2168 is effectively reduced.

In the present embodiment, the microscope container 2170 is taken in and out of the incubator 2164 by the slide device 2166, but the mechanism to take the microscope container 2170 in and out is not limited thereto, and any known moving mechanism is applicable. Moreover, the moving mechanism such as the slide device 2166 may be omitted, and the microscope container 2170 may be manually taken in and out of the incubator 2164.

In the present embodiment, the illumination device 2167 for the fluorescent observation is again the oblique illumination device, but may be the incident-light illumination device. That is, the illumination device 2167 for the fluorescent observation includes the objective lens 2174 and may have the configuration similar to those of the illumination devices described in the first embodiment to fourth embodiment.

While the embodiments of the present invention have been described above referring to the drawings, the present invention is not limited these embodiments, and various modifications and alterations may be made without departing from the sprit thereof.

The microscope device in the culture microscope apparatus is an inverted microscope in the above embodiments, but is not limited to it, that is, the microscope device may be an up-right microscope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. A culture microscope apparatus comprising:
   (i) an optical system for observing a specimen, the optical system including an objective lens to observe the specimen;
   (ii) a culture device defining at least three regions including:
      a region I where temperature and humidity are maintained at a level equal to that in an environment inside a body of a human being or an animal by the culture device,
      a region II, which is provided in a space not including the region I and adjacent to the region I, and where the temperature is on a level equal to that of the region I and the humidity is maintained at a normal humidity level by the culture device, and
      a region III, which is provided in a space under the region I and the region II and adjacent to the region II, on a normal temperature and normal humidity level outside of the culture device,
   wherein the specimen is located in the region I, and the objective lens extends through a boundary between the regions I and II; and
   (iii) a transparent optical member that is positioned on a boundary between the regions II and III, the transparent optical member being located on an optical axis of the optical system, so that light for the optical system passes through the boundary between the regions II and III.

2. The culture microscope apparatus according to claim 1, wherein the optical system includes an image pickup device for picking up an image of the specimen, and the image pickup device is located in the region III.

3. The culture microscope apparatus according to claim 2, wherein the regions I, II, and III are located along the optical axis of the optical system, and the specimen, the objective lens, and the image pickup device are located along the optical axis.

4. The culture microscope apparatus according to claim 2, wherein the regions I and II satisfy the following conditional equations:

$$36°\text{C.} \leq t1 \leq 38°\text{C.}, 90\% \leq h1 \leq 100\%$$

$$36°\text{C.} \leq t2 \leq 38°\text{C.}, 50\% \leq h2 \leq 80\%$$

where t1 indicates the temperature of the region I, h1 indicates the humidity of the region I, t2 indicates the temperature of the region II, and h2 indicates the humidity of the region II.

5. The culture microscope apparatus according to claim 1, wherein the regions I and II satisfy the following conditional equations:

$$36°\text{C.} \leq t1 \leq 38°\text{C.}, 90\% \leq h1 \leq 100\%$$

$$36°\text{C.} \leq t2 \leq 38°\text{C.}, 50\% \leq h2 \leq 80\%$$

where t1 indicates the temperature of the region I, h1 indicates the humidity of the region I, t2 indicates the temperature of the region II, and h2 indicates the humidity of the region II.

6. A culture microscope apparatus comprising:
(i) an optical system for observing a specimen, the optical system comprising an objective lens to observe the specimen, and an image pickup device to pick up an observation image of the specimen;
(ii) a culture device defining at least three regions including:
a region I where temperature and humidity are maintained at a level equal to that in an environment inside a body of a human being or an animal by the culture device,
a region II, which is provided in a space not including the region I and adjacent to the region I, and where the temperature is on a level equal to that of the region I and the humidity is maintained at a normal humidity level by the culture device, and
a region III, which is provided in a space under the region I and the region II and adjacent to the region II, on a normal temperature and normal humidity level outside of the culture device,
wherein the specimen is located in the region I, the objective lens extends through a boundary between the regions I and II, and the image pickup device is located in the region III.

7. The culture microscope apparatus according to claim 6, wherein the regions I and II satisfy the following conditional equations:

$$36°\text{C.} \leq t1 \leq 38°\text{C.}, 90\% \leq h1 \leq 100\%$$

$$36°\text{C.} \leq t2 \leq 38°\text{C.}, 50\% \leq h2 \leq 80\%$$

where t1 indicates the temperature of the region I, h1 indicates the humidity of the region I, t2 indicates the temperature of the region II, and h2 indicates the humidity of the region II.

\* \* \* \* \*